(12) United States Patent
Radhakrishna et al.

(10) Patent No.: US 10,204,703 B2
(45) Date of Patent: Feb. 12, 2019

(54) MEDICAL CODING MANAGEMENT SYSTEM USING AN INTELLIGENT CODING, REPORTING, AND ANALYTICS-FOCUSED TOOL

(71) Applicant: Accenture Global Services Limited, Dublin (IE)

(72) Inventors: Prathap Radhakrishna, Bangalore (IN); Shobhit Shrotriya, Bangalore (IN); Nagendra K. Kumar, Bangalore (IN)

(73) Assignee: Accenture Global Services Limited, Dublin (IE)

( * ) Notice: Subject to any disclaimer, the term of this patent is extended or adjusted under 35 U.S.C. 154(b) by 731 days.

(21) Appl. No.: 14/607,627

(22) Filed: Jan. 28, 2015

(65) Prior Publication Data
US 2016/0132643 A1    May 12, 2016

(30) Foreign Application Priority Data

Nov. 10, 2014    (IN) .......................... 5653/CHE/2014

(51) Int. Cl.
    *G16H 10/60*    (2018.01)
    *G06F 19/00*    (2018.01)
(52) U.S. Cl.
    CPC ............. *G16H 10/60* (2018.01); *G06F 19/00* (2013.01); *G06F 19/324* (2013.01)
(58) Field of Classification Search
    CPC ...... G06F 19/322; G06F 19/324; G16H 10/60
    See application file for complete search history.

(56) References Cited

U.S. PATENT DOCUMENTS

| 7,233,938 | B2 | 6/2007 | Carus et al. |
| 7,610,192 | B1* | 10/2009 | Jamieson ............ G06F 17/2229 704/1 |
| 8,731,966 | B2 | 5/2014 | Breitenstein et al. |

(Continued)

FOREIGN PATENT DOCUMENTS

EP    2290608    3/2011

OTHER PUBLICATIONS

Extended European Search Report corresponding to EP Application No. 15188911.0, dated Jun. 22, 2016, 9 pages.

(Continued)

*Primary Examiner* — Victoria P Shumate
*Assistant Examiner* — Chad A Newton
(74) *Attorney, Agent, or Firm* — Harrity & Harrity, LLP

(57) ABSTRACT

A device may receive information that identifies a first medical term and may determine whether the first medical term corresponds to a first medical code, which may be a medical code previously input by a first user in association with a second medical term. Or, the first medical code may be included in a dictionary. The device may determine a valid code corresponding to the first medical term based on determining whether the first medical term corresponds to the first medical code. The valid code may be determined based on the first medical code when the first medical term corresponds to the first medical code. The valid code may be determined based on a second medical code, input by a second user, when the first medical term does not correspond to the first medical code. The device may provide information that identifies the valid code.

20 Claims, 15 Drawing Sheets

(56) References Cited

U.S. PATENT DOCUMENTS

| | | | |
|---|---|---|---|
| 2003/0069760 A1* | 4/2003 | Gelber | G06Q 40/02 |
| | | | 705/4 |
| 2003/0167189 A1 | 9/2003 | Lutgen et al. | |
| 2011/0213557 A1* | 9/2011 | Kopta | G06F 19/363 |
| | | | 702/19 |
| 2011/0301982 A1* | 12/2011 | Green, Jr. | G06F 19/3443 |
| | | | 705/3 |
| 2013/0218598 A1 | 8/2013 | Aita et al. | |
| 2016/0210426 A1* | 7/2016 | Robinson | G06Q 50/24 |

OTHER PUBLICATIONS

Cerner, "Intelligent Coding, Dictionary Management dsNavigator," http://www.cerner.com/uploadedFiles/fl03_697_10_v2_dsNavigator_hr.pdf, Nov. 25, 2010, 1 page.

Oracle Health Sciences, "Oracle Health Sciences Central Coding," http://www.oracle.com/us/products/applications/health-sciences/e-clinical/central-coding/index.html, Nov. 20, 2012, 1 page.

Oracle Health Sciences, "Powering Clinical Studies with Oracle Clinical," http://www.oracle.com/us/industries/life-sciences/045788.pdf, May 27, 2010, 3 pages.

Medidata, "Medidata Coder: Cloud-Based Enterprise Coding Solution," https://aws-mdsol-corporate-website-prod.s3.amazonaws.com/CODR_Cloud-Based-Enterprise-Coding_20140122_Medidata_Fact-Sheet.pdf, Jan. 22, 2014, 2 pages.

Pace Computer Solutions, "Healthcare," http://pace-solutionsinc.com/Healthcare.html, Apr. 27, 2010, 2 pages.

* cited by examiner

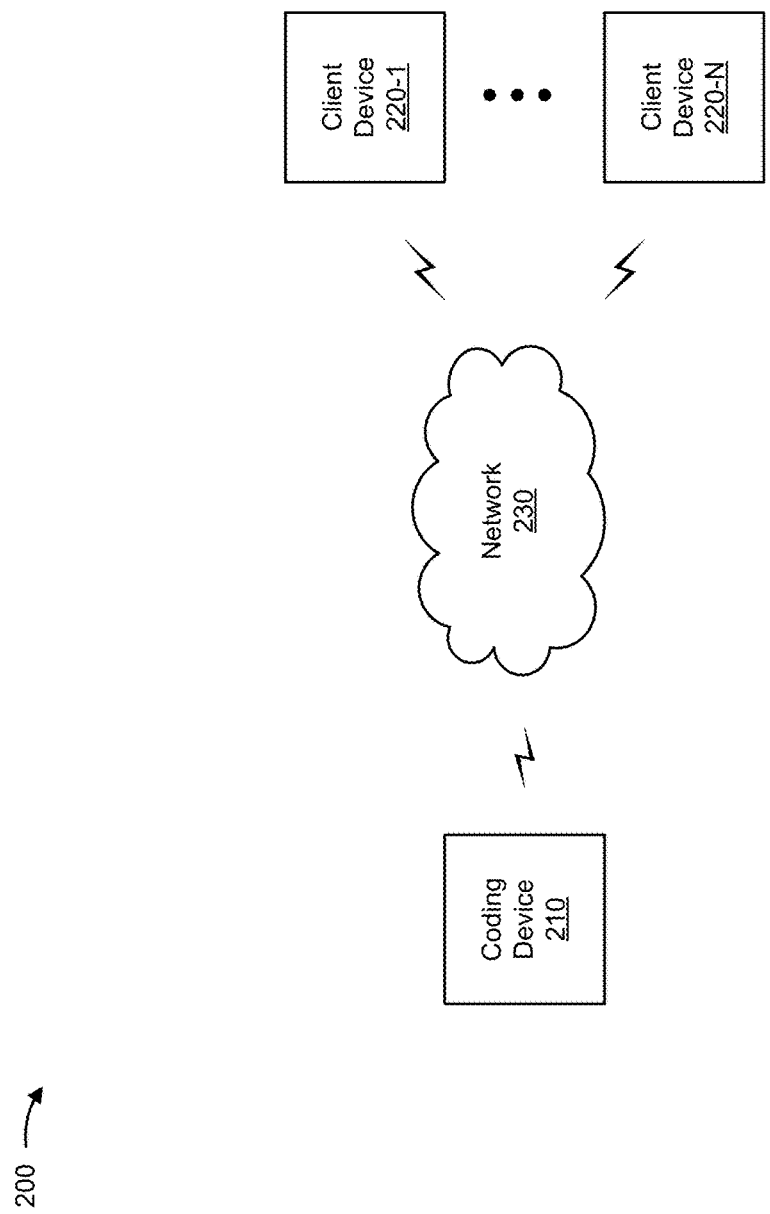

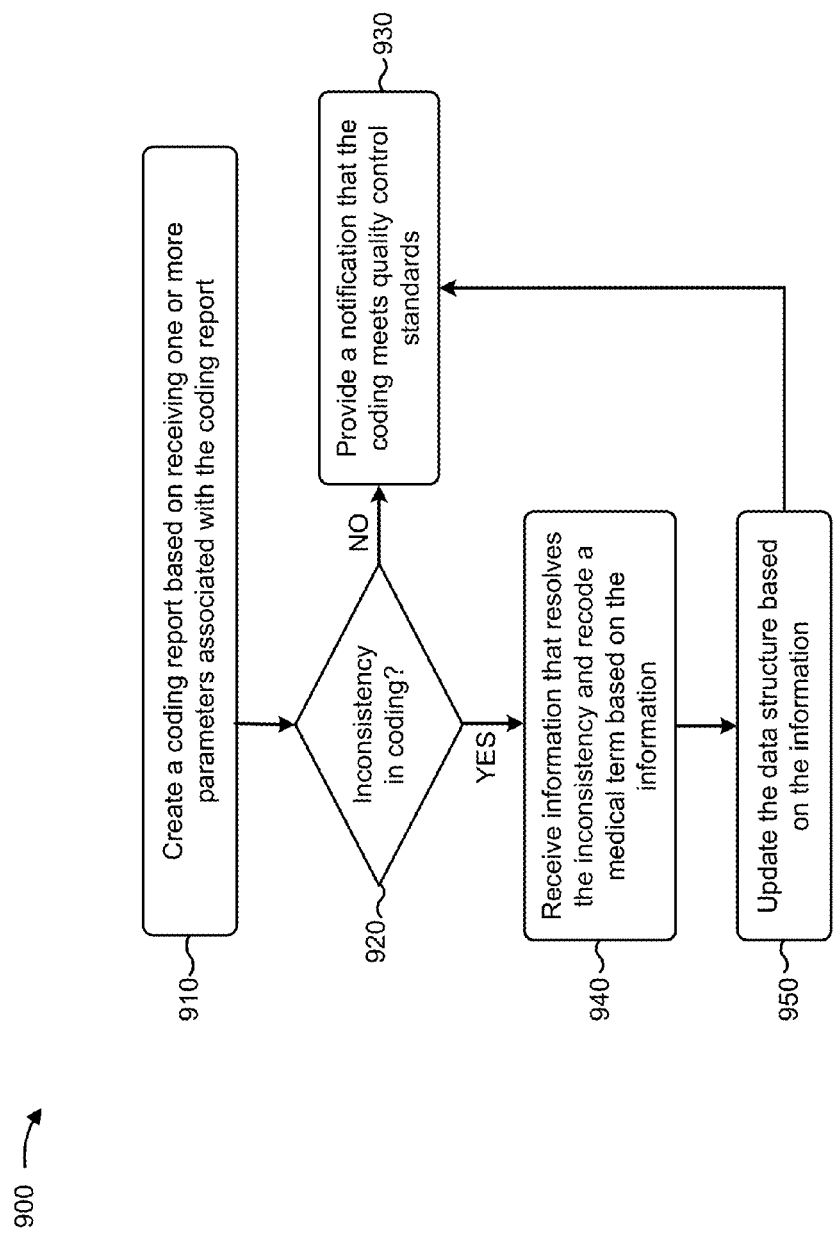

MEDICAL CODING MANAGEMENT SYSTEM USING AN INTELLIGENT CODING, REPORTING, AND ANALYTICS-FOCUSED TOOL

RELATED APPLICATION

This application claims priority under 35 U.S.C. § 119 to Indian Provisional Patent Application No. 5653/CHE/2014, filed on Nov. 10, 2014, the content of which is incorporated by reference herein in its entirety.

BACKGROUND

A medical dictionary may include standardized medical codes that may be used to communicate, in a standardized manner, data related to a medical product (e.g., data related to a drug). A medical code may represent or code a drug, an effect (e.g., a harmful effect resulting from a drug and/or other medical intervention or a positive effect resulting from a drug and/or other medical intervention), and/or information related to the drug and/or the effect.

SUMMARY

According to some possible implementations, a computer-readable medium may store instructions that, when executed by a processor, cause the processor to receive information that identifies a medical term. The instructions may cause the processor to determine whether the first medical term is associated with a first medical code. The first medical code may be a medical code previously input by a first user in association with a second medical term. Or, the first medical code may be included in a dictionary stored by a data structure. The instructions may cause the processor to determine a valid code associated with the first medical term based on determining whether the first medical term is associated with the first medical code. The valid code may be determined based on the first medical code when the first medical term is associated with the first medical code. The valid code may be determined based on a second medical code, input by a second user, when the first medical term is not associated with the first medical code. The instructions may cause the processor to provide information that identifies the valid code.

According to some possible implementations, a method may include receiving, by a device, information that identifies a first medical term. The method may include determining, by the device, whether the first medical term matches a second medical term, associated with a first medical code, or a second medical code. The first medical code may be a medical code previously input by a first user in association with the second medical term. The second medical code may be included in a dictionary stored by a data structure. The method may include determining, by the device, a valid code associated with the first medical term based on determining whether the first medical term matches the second medical term or the second medical code. The valid code may be determined based on the second medical term or the second medical code when the first medical term matches the second medical term or the second medical code. The valid code may be determined based on a third medical code, input by a second user, when the first medical term does not match the second medical term or the second medical code. The method may include providing, by the device, information that identifies the valid code.

According to some possible implementations, a device may include one or more processors. The one or more processors may receive information that identifies a first medical term. The one or more processors may determine whether the first medical term is associated with a first medical code. The first medical code may be a medical code previously input by a first user in association with a second medical term. Or, the first medical code may be included in a dictionary stored by a data structure. The one or more processors may determine a valid code associated with the first medical term based on determining whether the first medical term is associated with the first medical code. The valid code may be determined based on the first medical code when the first medical term is associated with the first medical code. The valid code may be determined based on a second medical code, input by a second user, when the first medical term is not associated with the first medical code. The one or more processors may provide information that identifies the valid code in association with the medical term.

BRIEF DESCRIPTION OF THE DRAWINGS

FIG. 2 is a diagram of an example environment in which systems and/or methods, described herein, may be implemented;

FIG. 9 is a flow chart of an example process for creating a coding report and/or updating the data structure based on the coding report.

DETAILED DESCRIPTION

The following detailed description of example implementations refers to the accompanying drawings. The same reference numbers in different drawings may identify the same or similar elements.

A medical dictionary (sometimes referred to herein as a dictionary) may be used in connection with a regulatory process of approving a medical product (e.g., pre-marketing activities, post-marketing activities, data entry, data retrieval, data evaluation, data presentation, etc). The medical dictionary may include medical codes that may improve consistency of terminology throughout different stages of development of a medical product, thereby allowing effective cross-referencing and analysis of data. A medical coding management system may assist in managing the medical dictionary and/or assigning a medical code to a medical term. A medical term may identify a drug, an effect, and/or information related to the drug and/or the effect. The medical dictionary and the medical term may be associated with a research study (e.g., a particular experiment or academic study performed to examine effects of a drug).

The medical coding management system may have shortcomings, such as: requiring manual set-up of a data structure associated with the research study, inability to update stored medical codes based on a dictionary update, inability to code based on context information associated with the medical term (e.g., route of entry of drug, purpose drug is used for, etc.), inability to selectively auto-code based on context information, inability to attach comments or queries to the medical term displayed via a user interface, inability to perform report analytics, inability to update the data structure based on the report analytics, or the like. As a result of these shortcomings, accuracy and consistency of medical coding may depend largely on experience of a user.

Implementations described herein may include a coding device that automatically creates and/or tests a data structure, that updates stored medical codes based on a dictionary update, that codes based on context information, that selectively auto-codes the medical term based on exact matching, that attaches comments or queries to the medical term provided via a user interface, that performs report analytics, and/or that updates the data structure based on the report analytics. Implementations described herein may improve accuracy and consistency of medical coding, thereby improving accuracy of medical records and improving public health.

Figure 1A:
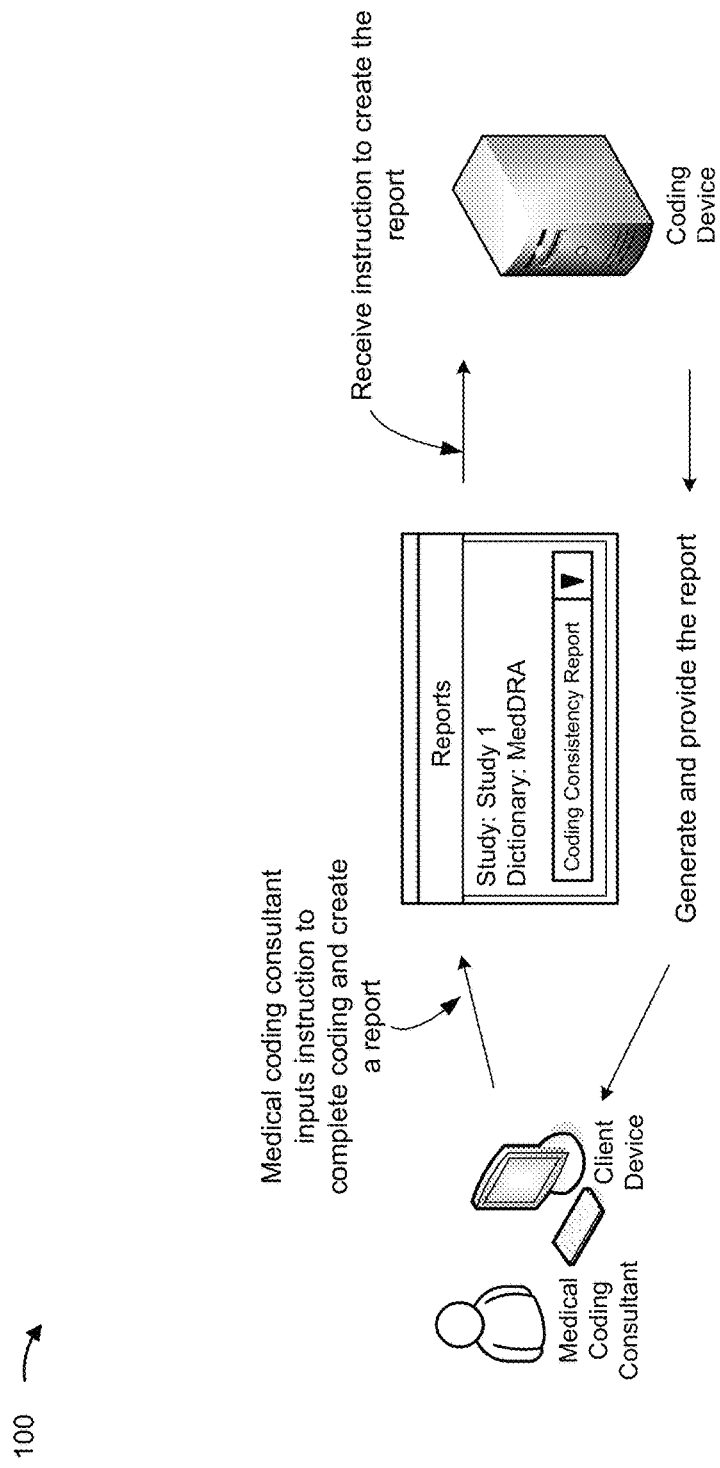
FIGS. 1A and 1B are diagrams of an overview of an example implementation described herein.
Figure 1B:
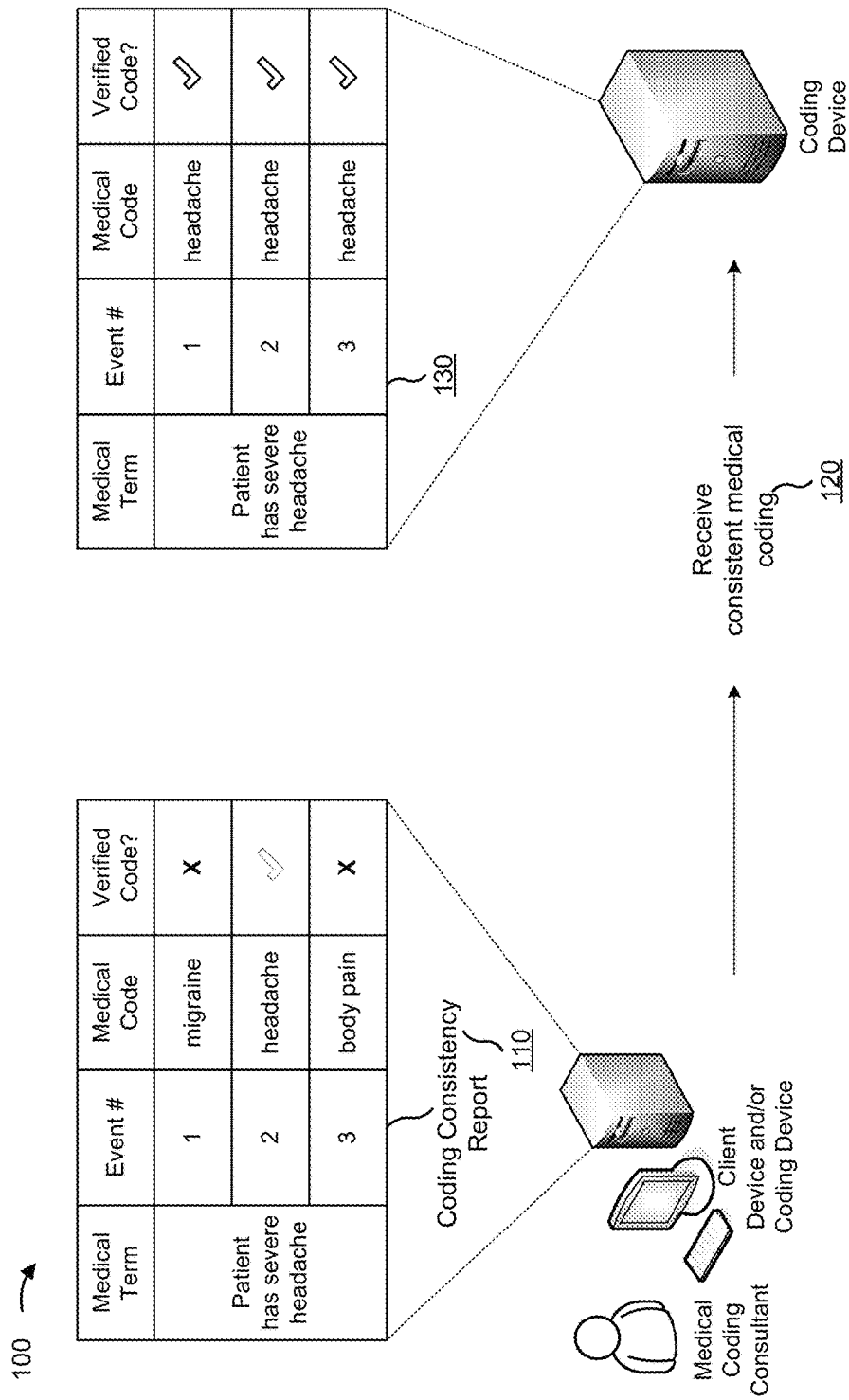

FIGS. 1A and 1B are diagrams of an overview of an example implementation 100 described herein. Assume that example implementation 100 includes a coding device (e.g., a server, a cloud storage device, a desktop computer, or the like) and a client device (e.g., a laptop computer, a desktop computer, or the like, that may provide a medical term to the coding device and that may display a user interface). Assume further that the coding device has created a data structure that may be used for storing medical term information that identifies a medical term. Assume further that the data structure is associated with a research study and a dictionary associated with the research study. Assume further that the coding device has determined, using automatic coding that uses exact matching and manual coding performed by a medical coder (e.g., a type of user), a medical code associated with the medical term.

As shown in FIG. 1A, the client device, upon receiving an instruction input by a medical coding consultant (e.g., another, more senior, type of user), may provide, to the coding device, an instruction to complete medical coding and to create a report. The instruction provided by the client device may identify a type of report (e.g., "Coding Consistency Report") that is to be created by the coding device. The client device, upon receiving an instruction from the medical coding consultant, may provide an instruction that identifies a research study (e.g., "Study 1") and a dictionary (e.g., "MedDRA," or Medical Dictionary for Regulatory Activities) associated with the coding consistency report. The coding consistency report may be a pre-configured report that assists in synchronizing medical coding performed by different medical coders, who may have coded a single medical term using different medical codes (e.g., because of human error). The coding device may receive the instruction to create the report. The coding device may determine whether there are inconsistencies in coding, and may generate the report. The coding device may provide the report, which identifies the inconsistencies in the coding, to the client device.

As shown in FIG. 1B, the client device may display the coding consistency report (e.g., as shown by reference number 110). The client device may display how a medical term "Patient has severe headache" occurs three times in the data structure and has been assigned a different medical code by a medical coder each time (e.g., migraine, headache, and body pain). A different medical code may have been assigned to a medical term by the medical coder because of human error.

The medical coding consultant, using his/her own expertise, may determine a verified medical code (e.g., a correct medical code, based on the circumstances of the research study, as determined by a medical coding consultant after analyzing a report), and input the verified medical code to the client device, which may provide the verified medical code to the coding device. As shown by reference number 120, the coding device may receive the verified medical code. Upon receiving the verified medical code, the coding device may store, in the data structure, the association between the verified medical code and the three instances of "Patient has severe headache" (e.g., as shown by reference number 130). In this way, the medical codes associated with the medical term may be synchronized by the medical coding consultant. In addition, the coding device may store the association between "Patient has severe headache" and "headache" as a medical coding consultant-approved association that may be used to automatically code the medical term "Patient has severe headache" (e.g., when the coding device next receives "Patient has severe headache" for coding).

In this way, the coding device may create a coding report, may receive information that resolves coding inconsistencies, may update the data structure accordingly, and may use the information that resolves coding inconsistencies during future instances of medical coding (e.g., such as during automatic coding or to provide a suggestion to the medical coder during manual coding). Implementations described herein may improve accuracy and consistency of medical coding, thereby improving the accuracy of medical records used during the drug-approval process, and thus, improving public health.

FIG. 2 is a diagram of an example environment 200 in which systems and/or methods, described herein, may be implemented. As shown in FIG. 2, environment 200 may include a coding device 210, one or more client devices 220-1 through 220-N (N≥1) (hereinafter referred to collectively as "client devices 220," and individually as "client device 220"), and network 230. Devices of environment 200 may interconnect via wired connections, wireless connections, or a combination of wired and wireless connections.

Coding device 210 may include one or more devices capable of receiving, storing, processing, and/or providing information. For example, coding device 210 may include a computing device, such as a server (e.g., a cloud-based server, an application server, a content server, a host server, a web server, etc.), a desktop computer, a laptop computer, or a similar device. In some implementations, coding device 210 may implement a medical coding management system. In some implementations, coding device 210 may create a data structure that may be used for storing medical term information that identifies a medical term. Additionally, or alternatively, coding device 210 may determine a medical code associated with a medical term (e.g., using automatic coding, manual coding without input from a medical coding consultant, and/or manual coding with input from a medical coding consultant). Additionally, or alternatively, coding device 210 may create a coding report and/or may update the data structure based on the coding report. In some implementations, coding device 210 may include a cloud server that is connected to one or more client devices 220 via network 230.

Client device 220 may include one or more devices capable of receiving, storing, processing, and/or providing information. For example, client device 220 may include a computing device, such as a laptop computer, a tablet computer, a handheld computer, a desktop computer, a mobile phone (e.g., a smart phone, a radiotelephone, etc.), or a similar device. In some implementations, client device 220 may display a user interface. Additionally, or alternatively, client device 220 may receive input from a user (e.g., a medical coder, a medical coding consultant, an administrator that controls user accounts used by a medical coder or a medical coding consultant and controls a level of access given to the user accounts, or some other type of user). Additionally, or alternatively, client device 220 may provide information to coding device 210 that corresponds to the input from the user.

In some implementations, client device 220 may receive input from the medical coder in connection with coding medical terms and/or creating a coding report. Additionally, or alternatively, client device 220 may receive input from the medical coding consultant in connection with providing medical term information for coding, creating one or more data structures associated with a research study, providing query information, performing dictionary updates, coding medical terms, and/or creating a coding report. Additionally, or alternatively, client device 220 may receive input from the administrator in connection with creating new users, managing the access accorded to users, and/or in connection with any activity that the medical coder or the medical coding consultant may perform. In some implementations, actions authorized for the medical coder, the medical coding consultant, and/or the administrator may be different than described above. Additionally, or alternatively, an action described below as performed by the medical coder, the medical coding consultant, and/or the administrator may be performed by any combination of the medical coder, the medical coding consultant, and/or the administrator.

Network 230 may include one or more wired and/or wireless networks. For example, network 230 may include a wireless local area network (WLAN), a local area network (LAN), a wide area network (WAN), a metropolitan area network (MAN), a telephone network (e.g., the Public Switched Telephone Network (PSTN)), a cellular network, a public land mobile network (PLMN), an ad hoc network, an intranet, the Internet, a fiber optic-based network, a cloud computing network, or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
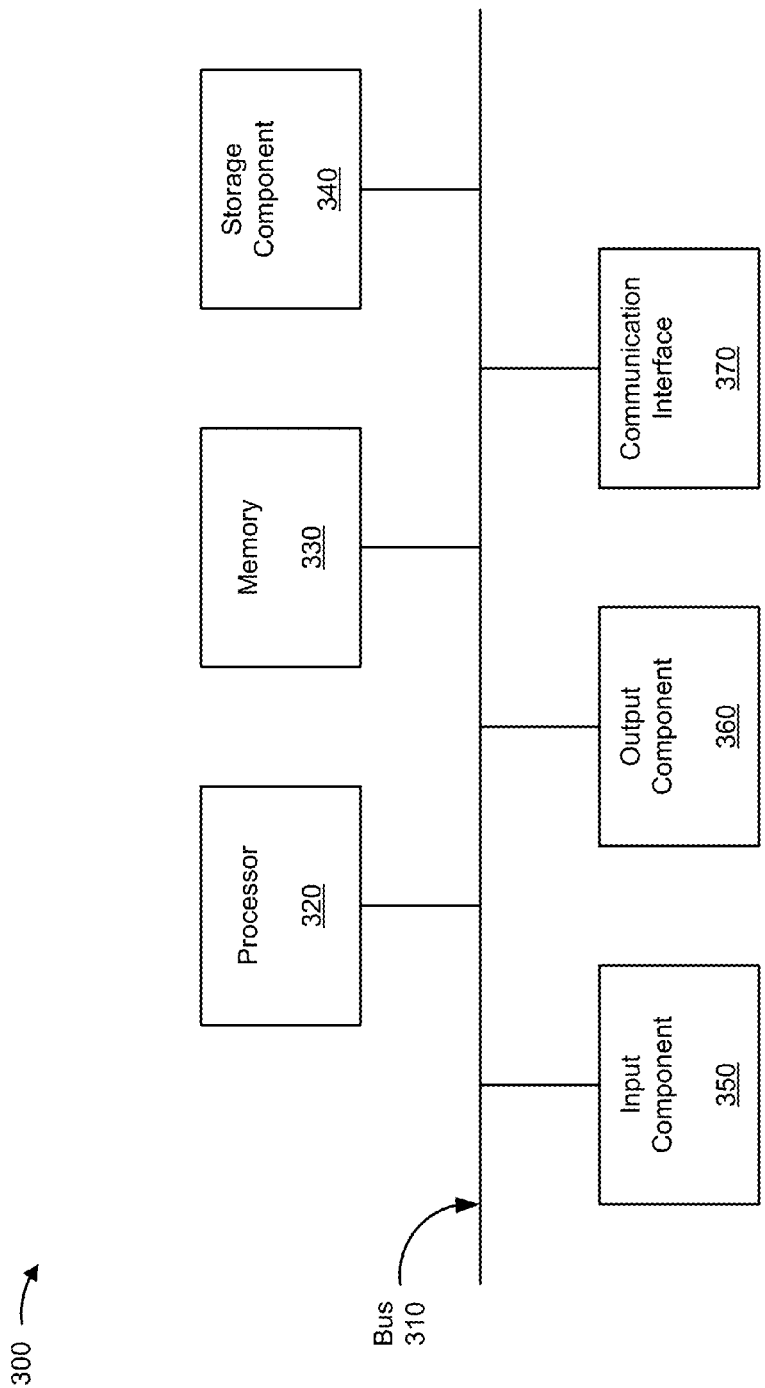
FIG. 3 is a diagram of example components of one or more devices of FIG. 2.

FIG. 3 is a diagram of example components of a device 300. Device 300 may correspond to coding device 210 and/or client device 220. In some implementations, coding device 210 and/or client device 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 may include a component that permits communication among the components of device 300. Processor 320 is implemented in hardware, firmware, or a combination of hardware and software. Processor 320 may include a processor (e.g., a central processing unit (CPU), a graphics processing unit (GPU), an accelerated processing unit (APU), etc.), a microprocessor, and/or any processing component (e.g., a field-programmable gate array (FPGA), an application-specific integrated circuit (ASIC), etc.) that interprets and/or executes instructions. Memory 330 may include a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 may store information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 350 may include a component that permits device 300 to receive information, such as via user input (e.g., a touch screen display, a keyboard, a keypad, a mouse, a button, a switch, a microphone, etc.). Additionally, or alternatively, input component 350 may include a sensor for sensing information (e.g., a global positioning system (GPS) component, an accelerometer, a gyroscope, an actuator, etc.). Output component 360 may include a component that provides output information from device 300 (e.g., a display, a speaker, one or more light-emitting diodes (LEDs), etc.).

Communication interface 370 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
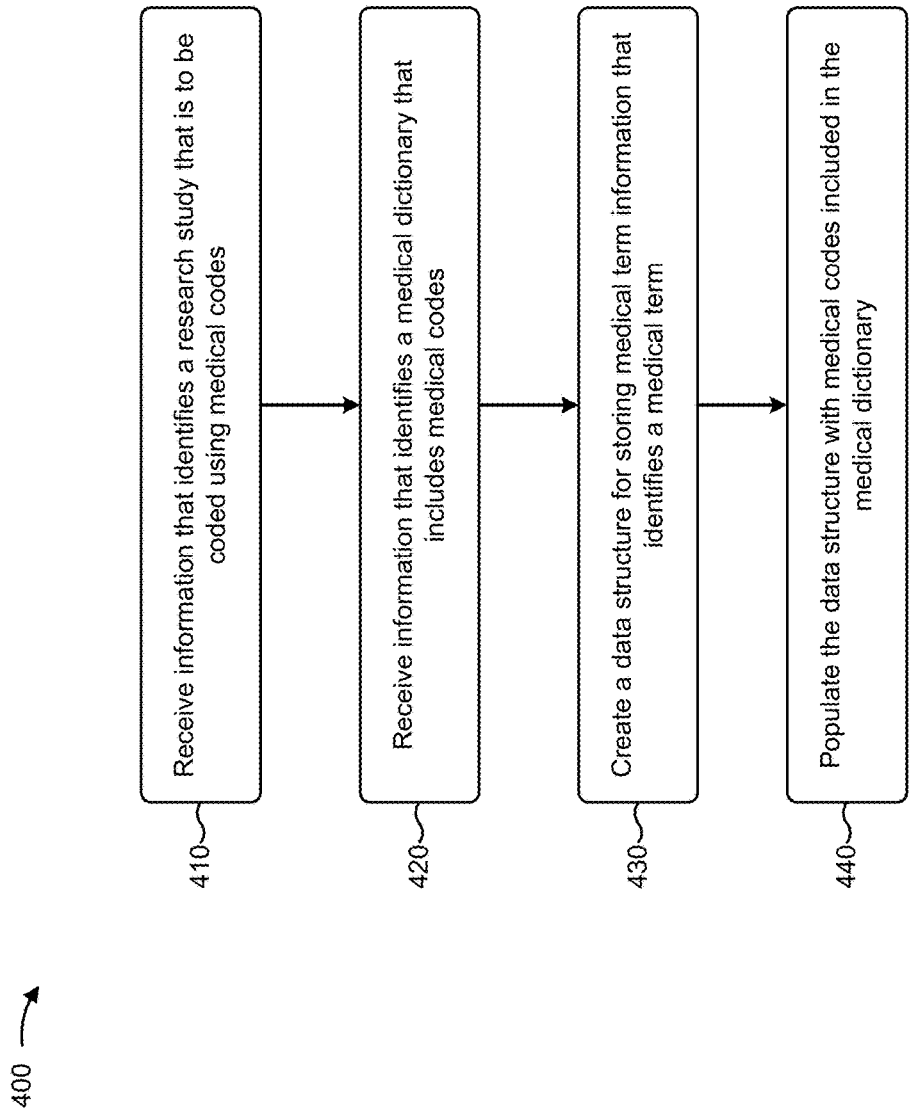
FIG. 4 is a flow chart of an example process for creating a data structure for storing medical term information that identifies a medical term.

FIG. 4 is a flow chart of an example process 400 for creating a data structure that may be used for storing medical term information that identifies a medical term. In some implementations, one or more process blocks of FIG. 4 may be performed by coding device 210. In some implementations, one or more process blocks of FIG. 4 may be performed by another device or a set of devices separate from or including coding device 210, such as client device 220.

As shown in FIG. 4, process 400 may include receiving information that identifies a research study that is to be coded using medical codes (block 410). For example, coding device 210 may receive information that identifies a research study that is to be coded using medical codes. In some implementations, client device 220 may receive an input from a medical coding consultant and, based on the input, may provide information that identifies the research study to coding device 210.

In some implementations, the research study may include an experiment and/or an academic inquiry into a drug's effects on human beings. Additionally, or alternatively, the medical coding consultant may input the information that identifies the research study when the experiment and/or the academic inquiry is to begin (e.g., so that coding device 210 can create a data structure for storing medical term information collected during the experiment and/or the academic inquiry). For example, the medical coding consultant may input the name "aspirin research study" to client device 220, which may provide the name "aspirin research study" to coding device 210.

In some implementations, the research study may be coded because medical terms included in the research study may need to be standardized in order to ease comparison of data from other research studies. Medical terms included in the medical term information may include the name of a drug used during the research study, an effect that a drug has on a patient (e.g., observed during the research study), and/or information related to the drug and/or the effect. Standardization of medical terms may be useful because different research studies may describe a drug or an effect using slightly different language, which may pose difficulties in comparing research studies (e.g., one research study may describe a patient that feels pain near a forehead as a "migraine," whereas another research study may describe a patient that feels pain near a forehead as a "headache").

Medical codes included in a medical dictionary may be used to standardize the medical terms. A medical code may represent or "code" a medical term. A medical dictionary may be issued by a regulatory authority, an academic committee charged with standardizing medical terms, or the like. For example, a regulatory authority may decree that the medical code "headache" should always be used when describing a patient that feels pain near a forehead (e.g., in this example, a medical term is "patient that feels pain near a forehead," and the corresponding medical code is "headache").

A medical coding management system (such as coding device 210 described herein) may assist in managing a medical dictionary and/or assigning a medical code to a medical term. In some implementations, coding device 210 may determine a medical code corresponding to a medical term automatically (e.g., based on a stored medical dictionary and/or based on intelligence acquired through previous instances of coding), may determine a medical code corresponding to a medical term based on manual input (e.g., with the assistance of input from a medical coder), and/or may determine a medical code corresponding to a medical term using query information (e.g., with the assistance of input from a medical coding consultant).

In some implementations, coding device 210 may perform medical coding in connection with multiple research studies. Coding device 210 may use information that identifies a research study to create a file for the research study (e.g., a file, stored by a data structure of coding device 210, which helps organize medical coding associated with a particular research study, and which helps prevent mixing and/or confusion with medical coding being performed in connection with other research studies).

In some implementations, information that identifies a research study may include a string that indicates the type of research study being conducted. For example, a research study name that includes "aspirin," "acetaminophen," or any other pain reliever, may be an indication that the type of research study being conducted is a pain relief research study. Additionally, or alternatively, the medical coding consultant may input to client device 220, and client device 220 may provide to coding device 210, an instruction that indicates the type of research study. For example, the coding device may receive "experiment15" for research study name and receive "longitudinal study" as the instruction that indicates the type of research study.

As further shown in FIG. 4, process 400 may include receiving information that identifies a medical dictionary that includes medical codes (block 420). For example, coding device 210 may receive information that identifies a medical dictionary that includes medical codes. In some implementations, client device 220 may receive an input from a medical coding consultant and, based on the input, may provide information that identifies the dictionary to coding device 210. For example, coding device 210 may receive information that identifies "MedDRA," or "World Health Organization Drug Dictionary" (WHO-DRUG Dictionary) as medical dictionaries for coding medical terms associated with the research study.

Additionally, or alternatively, coding device 210 may receive information that identifies a customized dictionary that is customized according to a user's specifications. The customized dictionary may be based on a standard dictionary, such as MedDRA (e.g., the user may have changed parts of the standard dictionary to make the standard dictionary a better fit for a type of medical research the user undertakes). In some implementations, the user may input an instruction to client device 220, which may provide a customized dictionary and/or which may provide a location of a customized dictionary that is pre-configured on coding device 210.

As further shown in FIG. 4, process 400 may include creating a data structure for storing medical term information that identifies a medical term (block 430). For example, coding device 210 may create a data structure for storing medical term information that identifies a medical term. In some implementations, coding device 210 may create the data structure based on the information that identifies the research study and based on the information that identifies the dictionary. Additionally, or alternatively, the data structure may be used for storing medical term information that is received as described below in connection with FIG. 6 (e.g., information that identifies a medical term, included in a research study, to be coded by coding device 210).

In some implementations, coding device 210 may create tables, views, stored procedures, and/or functions associated with the data structure based on the information that identifies the research study and/or based on the information that identifies the dictionary. Additionally, or alternatively, manual set up of the data structure may not be necessary, as coding device 210 may automatically create the data structure (e.g., coding device 210 may create tables, views, stored procedures, and/or functions of the data structure without manual input originating from the user). Additionally, or alternatively, coding device 210 may perform automatic user-acceptance testing in association with the data structure. For example coding device 210 may test the data structure using sample data associated with the data structure. In some implementations, automatic set up of the data structure and automatic testing of the data structure may save time compared to performing a manual set up and/or a manual user-acceptance test.

In some implementations, coding device 210 may create the data structure based on receiving an instruction from client device 220, which may have received an instruction from a medical coding consultant using a one-click process. For example, the medical coding consultant may interact with an input mechanism (e.g., a button, a link, etc.) displayed on a user interface of client device 220 to cause client device 220 to provide an instruction to coding device 210, which may create the data structure (e.g., including the automatic set up and the automatic testing).

In some implementations, coding device 210 may create the data structure in a manner that allows the data structure to store context information that is associated with a medical term. For example, coding device 210 may create the data structure in a manner that allows the data structure to store information that identifies a route of entry of a drug (e.g., orally, via a suppository, via a skin patch, via inhalation, or the like), a time of day the drug was taken, a purpose of taking the drug (e.g., acetaminophen being used as a pain reliever or acetaminophen being used as a fever reducer), a dosage of the drug, or the like.

In some implementations, coding device 210 may create the data structure using a relational database model (e.g., a model that organizes data into one or more tables (or "relations") of rows and columns, with a unique key for each row, and where the unique key of a row is used to relate a row to another row). Additionally, or alternatively, coding device 210 may create the data structure using another type of database and/or another form of arrangement of data.

In some implementations, coding device 210 may create the same data structure for every research study identified by client device 220. Additionally, or alternatively, coding device 210 may create a different data structure based on a research study name (e.g., coding device 210 may be pre-configured to create a particular data structure if a particular research study name is input into client device 220 and provided to coding device 210). For example, if the research study name contains "aspirin," "acetaminophen," or the name of any other pain reliever, coding device 210 may create a data structure capable of storing information related to the level of pain a patient is experiencing based on a pain scale. Additionally, or alternatively, coding device 210 may create the data structure based on a type of research study being conducted. For example, coding device 210 may create a data structure capable of storing patient information as a function of time if coding device 210 receives an instruction that the research study is a longitudinal study.

As further shown in FIG. 4, process 400 may include populating the data structure with medical codes included in the medical dictionary (block 440). For example, coding device 210 may populate the data structure with medical codes included in the medical dictionary. For example, coding device 210 may populate the data structure with medical codes included in MedDRA, WHO-DRUG Dictionary, a customized dictionary, or the like. In some implementations, coding device 210 may use the medical codes used to populate the data structure to code medical terms received during a process described below in connection with FIG. 6.

In some implementations, coding device 210 may receive a dictionary update (e.g., information that identifies a new version of a medical dictionary and/or the contents of the new version of the medical dictionary). The contents of the new version of the medical dictionary may include medical codes newly agreed upon by regulatory authorities. In some implementations, coding device 210 may detect that a new version of the medical dictionary is available and may retrieve the dictionary update (e.g., the new version of the medical dictionary may be released by a regulatory authority, an international medical coding organization, or the like). Additionally, or alternatively, coding device 210 may receive the dictionary update from client device 220 (e.g., because of an input by the user), or from another device.

In some implementations, as a result of receiving the dictionary update, coding device 210 may use the updated dictionary when determining whether the medical term can be automatically coded and/or may use the updated dictionary when determining a valid code associated with the medical term (as described below in connection with FIG. 6). In some implementations, automatically detecting and/or using the dictionary update allows coding device 210 to code a medical term according to the latest demands of a regulatory authority. Additionally, or alternatively, coding device 210 may receive and/or retrieve the dictionary update at regular intervals of time.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
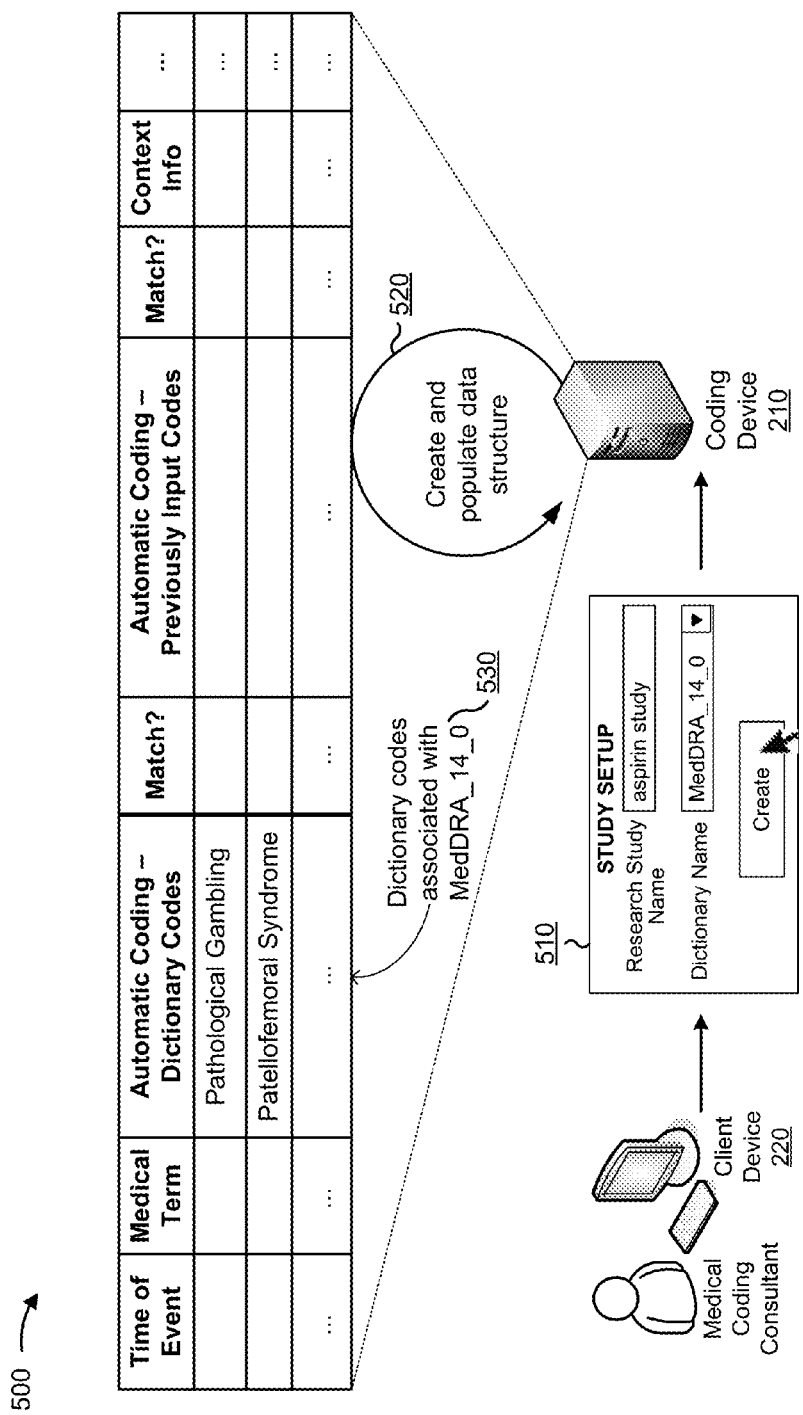
FIG. 5 is a diagram of an example implementation relating to the example process shown in FIG. 4.

FIG. 5 is a diagram of an example implementation 500 relating to example process 400 shown in FIG. 4. FIG. 5 shows an example of creating a data structure that may be used for storing medical term information that identifies a medical term.

As shown in FIG. 5, assume that example implementation 500 includes coding device 210 and client device 220. A medical coding consultant interacts with a user interface displayed on client device 220, which allows the medical coding consultant to input information that identifies a research study and information that identifies a medical dictionary. As shown by reference number 510, the medical coding consultant clicks on the "create" button on the user interface after inputting the research study name and the dictionary name. As shown, coding device 210 receives information that identifies the research study (e.g., information that indicates that the research study's name is "aspirin study") from client device 220. As further shown by reference number 510, coding device 210 receives information that identifies a dictionary (e.g., information that indicates that the dictionary's name is "MedDRA_14_0," which may represent the 2014 version of the MedDRA dictionary).

Coding device 210 determines the features of the data structure based on pre-configured settings and based on the information that identifies the research study and the information that identifies the dictionary. Assume that the pre-configured settings indicate that any research study name that includes "aspirin" should correspond to a data structure capable of storing information that identifies a time of an event (e.g., a time when a medical term was observed during the research study), a medical term, dictionary codes, previously input codes, context information such as route of entry and/or purpose of drug, or the like. As shown by reference number 520, coding device 210 creates a data structure for storing information that identifies the time of the event, the medical term, dictionary codes, previously input codes, context information, or the like. Coding device 210 creates the data structure as a result of the one-click "create" instruction that medical coding consultant provided to client device 220, which sent the "create" instruction to coding device 210.

As further shown, coding device 210 populates the data structure with medical codes included in the medical dictionary (e.g., medical codes included in MedDRA, as shown by reference number 530). As shown, the medical codes included in the medical dictionary include "Pathological Gambling," "Patellofemoral Syndrome," or the like. The data structure created by coding device 210 is specific to aspirin study and specific to a 2014 version of MedDRA (e.g., coding device 210 creates a different data structure for each research study and/or each dictionary associated with each research study in order to organize coding being performed in connection with multiple research studies and multiple associated dictionaries). Coding device 210 may use the medical codes, used to populate the data structure, to code medical terms received as described below in connection with FIG. 6 (e.g., to code medical terms, associated with the research study, when the medical terms are loaded into coding device 210).

As indicated above, FIG. 5 is provided merely as an example. Other examples are possible and may differ from what was described with regard to FIG. 5.

Figure 6:
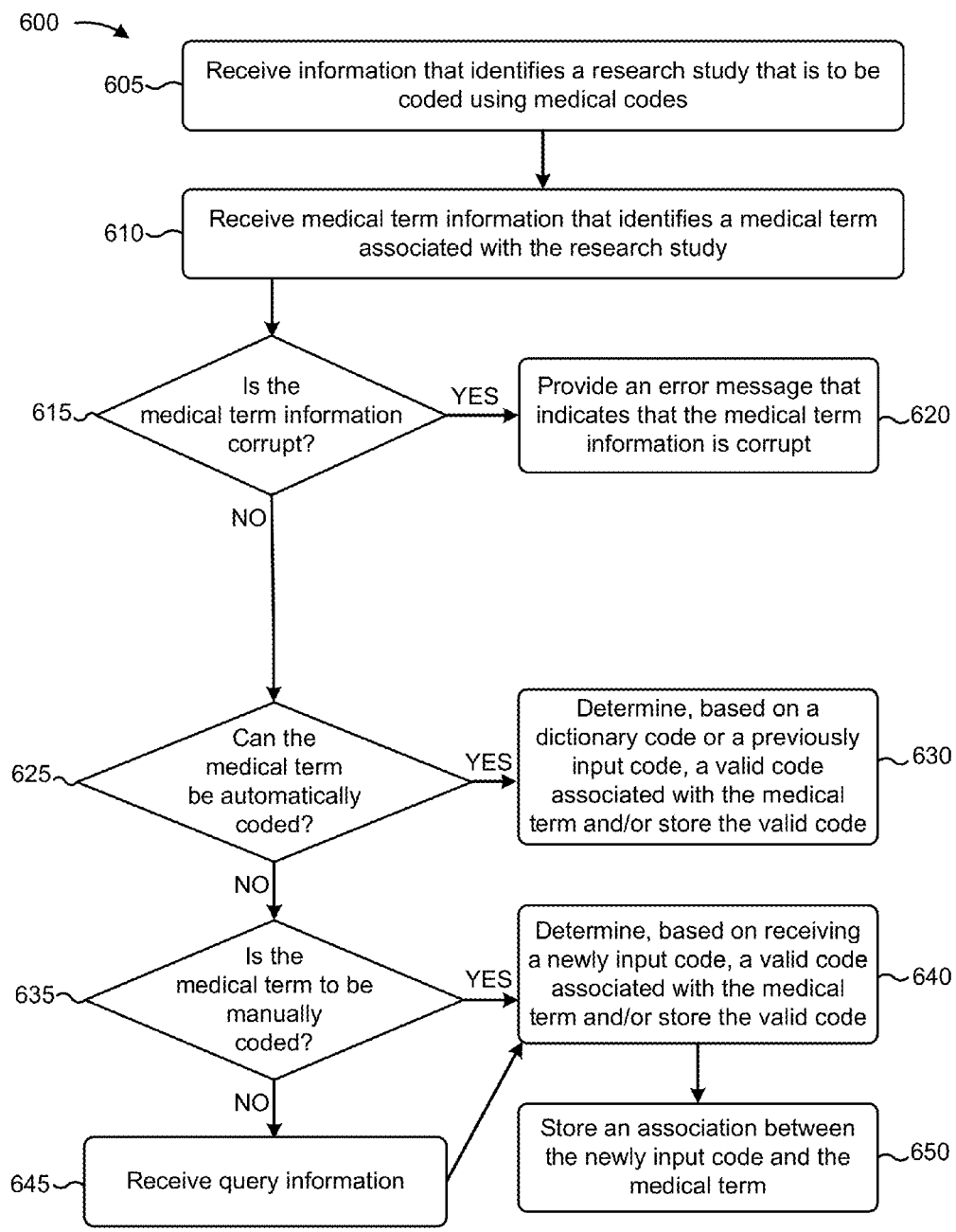
FIG. 6 is a flow chart of an example process for determining a medical code associated with a medical term and/or storing the medical code in the data structure.

FIG. 6 is a flow chart of an example process 600 for determining a medical code associated with a medical term and/or storing the medical code in the data structure. In some implementations, one or more process blocks of FIG. 6 may be performed by coding device 210. In some implementations, one or more process blocks of FIG. 6 may be performed by another device or a set of devices separate from or including coding device 210, such as client device 220.

As shown in FIG. 6, process 600 may include receiving information that identifies a research study that is to be coded using medical codes (block 605). For example, coding device 210 may receive information that identifies a research study that is to be coded using medical codes. In some implementations, coding device 210 may receive information that identifies a research study from client device 220, which may have received an input from a user (e.g., a medical coder) that identifies a research study. For example, a user may input a research study name "aspirin study" to client device 220, which may provide the research study name to coding device 210. A user may input "aspirin study" to alert coding device 210 that coding device 210 will soon receive medical term information that identifies a medical term associated with the aspirin study (e.g., a medical coder will soon load medical terms observed during the aspirin study into coding device 210, so that coding device 210 can assist in assigning medical codes to the medical terms).

In some implementations, coding device 210 may store one or more data structures associated with one or more research studies (e.g., data structures that may have been created for the research studies as described above in connection with FIG. 4). Additionally, or alternatively, coding device 210 may use the information that identifies the research study to open and/or configure a data structure associated with the research study (e.g., to choose a particular data structure out of data structures stored by coding device 210). For example, coding device 210 may open and/or configure a data structure associated with the aspirin study if coding device 210 receives information that identifies the aspirin study. Additionally, or alternatively, coding device 210 may prepare the data structure for receiving data.

As further shown in FIG. 6, process 600 may include receiving medical term information that identifies a medical term associated with the research study (block 610). For example, coding device 210 may receive medical term information that identifies a medical term associated with the research study. For example, coding device 210 may receive medical term information that identifies the following medical terms in connection with the aspirin study: "patient feels pain," "patient has had a heart attack," "the guy keeled over at 10 PM," "acetylsalicylic acid, orally," etc. These medical terms may be coded using standardized medical codes, as described herein.

In some implementations, coding device 210 may receive medical term information from client device 220. Additionally, or alternatively, coding device 210 may receive medical term information from a location identified by an instruction from client device 220. In some implementations, client device 220 may provide the instruction to coding device 210 based on an input received from a user. In some implementations, coding device 210 may receive medical term information that includes context information such as a route of entry of a drug, a purpose of the drug, a dosage of the drug, or the like.

In some implementations, coding device 210 may store the medical term information in a preliminary location within the data structure to protect medical term information already stored by the data structure from the possibility of being corrupted by newly received medical term information (e.g., since the medical term information has not been tested for corrupt data yet). Additionally, or alternatively, coding device 210 may store the medical term information in an encrypted form to improve security of medical records.

In some implementations, coding device 210 may receive and/or retrieve the medical term information based on whether an amount of time that has passed since medical term information was last received satisfies a threshold. For example, coding device 210 may retrieve, from a pre-configured location, medical term information every 24 hours, every 48 hours, every week, or the like.

Additionally, or alternatively, coding device 210 may receive and/or retrieve the medical term information based on whether a volume of available medical term information satisfies a threshold. For example, coding device 210 may retrieve, from a pre-configured location, medical term information when there is at least a particular quantity (e.g., five, ten, fifty, etc.) of new medical terms associated with the pre-configured location.

As further shown in FIG. 6, process 600 may include determining whether the medical term information is corrupt (block 615). For example, coding device 210 may determine whether the medical term information includes corrupt data (e.g., data that does not conform to the formatting guidelines expected for the data or data that is unsuitable for coding in some other way). In some implementations, coding device 210 may determine whether the medical term information includes corrupt data based on formatting guidelines expected for the data and/or received from client device 220. Additionally, or alternatively, client device 220 may have provided formatting guidelines, associated with the research study, to coding device 210. Checking the medical term information for corrupted data before coding prevents corrupted medical term information from contaminating medical term information that has already been coded and/or prevents corrupted medical term information from contaminating other data stored by coding device 210.

As further shown in FIG. 6, if the medical term information is corrupt (block 615—YES), then process 600 may include providing an error message that indicates that the medical term information is corrupt (block 620). For example, if coding device 210 determines that the medical term information includes corrupted data, coding device 210 may provide an error message that indicates that the medical term information is corrupt. In some implementations, coding device 210 may provide the error message to client device 220, which may display the error message on a user interface.

In some implementations, coding device 210 may provide a list of corrupted medical terms included in the medical term information and may provide the location of the corrupted medical terms within the medical term information. Additionally, or alternatively, coding device 210 may allow the user, through the user interface of client device 220, to change the formatting of corrupted medical terms or otherwise make the corrupted medical terms non-corrupt. In some implementations, coding device 210 may provide the corrupted medical terms that have been made non-corrupt to the data structure for coding.

As further shown in FIG. 6, if the medical term information is not corrupt (block 615—NO), then process 600 may include determining whether the medical term can be automatically coded (block 625). For example, coding device 210 may determine whether the medical term can be automatically coded. In some implementations, coding device 210 may move the medical term information from the preliminary location within the data structure (e.g., where the medical term information was kept to prevent contamination until coding device 210 determined the medical term information to be non-corrupt) to elsewhere in the data structure to begin the coding process.

Coding device 210 may determine whether the medical term can be automatically coded based on determining whether the medical term is associated with a dictionary code or a previously input code. A dictionary code may include a medical code included in the dictionary identified as described above in connection with FIG. 4 and stored by the data structure. A previously input code may include a medical code input by a user, in association with a previously received medical term, during a previous coding process. For example, a user may have input the medical code "headache" in association with the medical term "Patient has severe headache" during a previous iteration of the coding process. The medical code "headache," in association with the medical term "Patient has severe headache," may have been stored by the data structure as a previously input code.

In some implementations, coding device 210 may determine whether the medical term can be automatically coded based on determining whether the medical term matches a dictionary code. Additionally, or alternatively, coding device 210 may determine whether the medical term can be automatically coded based on determining whether the medical term matches a previous medical term associated with a previously input code. If the medical term does not match the dictionary code and the medical term does not match the previous medical term associated with the previously input code, coding device 210 may determine that the medical term cannot be automatically coded. If the medical term matches the dictionary code or the medical term matches the previous medical term associated with the previously input code, coding device 210 may determine that the medical term can be automatically coded.

In some implementations, coding device 210 may determine whether the medical term can be automatically coded based on receiving an instruction from client device 220, which may be based on input from the user. For example, the user may decide to not use automatic coding and may input this decision via the user interface of client device 220, which may forward an instruction to not use automatic coding to coding device 210.

As further shown in FIG. 6, if the medical term can be automatically coded (block 625—YES), then process 600 may include determining, based on a dictionary code or a previously input code, a valid code associated with the medical term and/or storing the valid code (block 630). For example, if the medical term can be automatically coded, coding device 210 may determine a valid code associated with the medical term and may store, in the data structure, the valid code in association with the medical term. A valid code may refer to a medical code that corresponds to the medical term as determined by automatic coding and/or by manual coding without using report analytics (on the other hand, a medical coding consultant may choose a correct valid code (e.g., a verified report) chosen after viewing a report, as described below in connection with FIG. 9).

In some implementations, coding device 210 may determine a valid code associated with the medical term based on a dictionary code and/or a previously input code. For example, coding device 210 may determine that a dictionary code matches the medical term, and may determine that the dictionary code is the valid code. As another example, coding device 210 may determine that a previous medical term associated with a previously input code matches the medical term, and may determine that the previously input code is the valid code.

In some implementations, coding device 210 may not consider probabilities of the medical term matching the dictionary code when determining the valid code (e.g., coding device 210 may seek an exact match in the dictionary instead of determining probable matches). Additionally, or alternatively, coding device 210 may not consider probabilities of the medical term matching the previous medical term associated with the previously input code when determining the valid code (e.g., coding device 210 may seek an exact match instead of determining probable matches). In some implementations, coding device 210 may seek an exact match because determining the valid code using probabilities may lead to a level of error in determining valid codes that is unacceptable in a regulatory context.

Additionally, or alternatively, coding device 210 may declare a match if a dictionary code and/or a previous medical term is sufficiently similar to a medical term (e.g., an inexact match with a medical term that is sufficiently similar to an exact match that a probability that the inexact match is a genuine match satisfies a threshold probability such as 80%, 90%, 99.99%, or the like). In some implementations, the threshold probability required to declare a match may be based on the type of research study, the dictionary, or the like. However, in some cases, using a threshold probability to declare a match may result in more errors in medical coding compared to using an exact match. Thus, in some implementations, coding device 210 may not use a threshold probability to declare a match and may seek an exact match (e.g., a 100% match).

In some implementations, coding device 210 may store, in the data structure, the valid code in association with the medical term. Additionally, or alternatively, coding device 210 may, during the dictionary update, update the data structure by replacing a valid code based on the dictionary code with a valid code based on a new dictionary code. Additionally, or alternatively, coding device 210 may, during the dictionary update, update the data structure by replacing a valid code based on the previously input code with a valid code based on a new dictionary code that corresponds to the previously input code.

In other words, coding device 210 may update the data structure by replacing previously input codes with medical codes included in the dictionary update (e.g., if a previously input code corresponds to a medical code included in the dictionary update). In some implementations, a dictionary update that incorporates previously input codes may result in better reporting analytics (e.g., because a standardized medical code included in the dictionary update may be easier to search for and/or compare with other medical codes in the data structure than a previously input code that has no links to a dictionary).

As further shown in FIG. 6, if the medical term cannot be automatically coded (block 625—NO), then process 600 may include determining whether the medical term is to be manually coded without input from a medical coding consultant (block 635). For example, coding device 210 may determine whether the medical term is to be manually coded without input from a medical coding consultant based on receiving an instruction from client device 220. A medical coding consultant may be a user that has a higher level of access permission and/or expertise than a medical coder. In some implementations, coding device 210 may receive an instruction that specifies that the medical coder has decided that coding device 210 is to perform manual coding. For example, the medical coder may determine that the medical coder is able to input, based on the medical coder's own expertise, a medical code associated with the medical term. In such an example, the medical coder may input an instruction that selects manual coding to client device 220, which may provide the instruction to coding device 210.

In some implementations, the medical coder may use a search tool included in coding device 210 (e.g., and displayed on the user interface of client device 220) to assist in determining whether the medical term is to be manually coded without input from the medical coding consultant. The search tool may include searching capabilities that allow the medical coder (or any other authorized user) to search previous medical terms using search inputs that are nearly identical to the medical term currently being coded. For example, the medical coder may search for "Patient has pain in head" if the medical term currently being coded is "Patient has pain in head." Additionally, or alternatively, the search tool may include the capability to search using an "and/or" input, the capability to simultaneously search for different strings included in different columns of the data structure, or the like.

As further shown in FIG. 6, if the medical term is to be manually coded without input from the medical coding consultant (block 635—YES), then process 600 may include determining, based on receiving a newly input code, a valid code associated with the medical term and/or storing the valid code (block 640), and storing an association between the newly input code and the medical term (block 650). For example, coding device 210 may receive a newly input code from client device 220, which may have received an input from the medical coder that specifies the newly input code (e.g., the newly input code that is the valid code may be "Nausea" if the medical term was "Patient feels queasy"). In some implementations, the medical coder may input the newly input code based on his/her own expertise in assigning medical codes for medical terms. Additionally, or alternatively, the medical coder may input the newly input code based on reading query information displayed on client device 220 (as described below in connection with block 645).

In some implementations, coding device 210 may store the association between the newly input code and the medical term for use in future iterations of process 600. In some implementations, the newly input code may be based on the medical coder's expertise (e.g., if the medical term was manually coded without input from the medical coding consultant). Additionally, or alternatively, the newly input code may be based on the medical coding consultant's expertise (e.g., if the medical term was coded based on receiving the query information). During future iterations of process 600 (e.g., when new medical term information is received by coding device 210), the association between the newly input code and the medical term may be used during automatic coding as described above in connection with block 625 of FIG. 6.

As further shown in FIG. 6, if the medical term is not to be manually coded without input from the medical coding consultant (block 635—NO), then process 600 may include receiving query information (block 645). For example, coding device 210 may receive query information from client device 220, which may have received an input from the medical coding consultant that includes the query information. In some implementations, coding device 210 may receive query information in response to a query initiated by a medical coder (e.g., the medical coder, via the user interface of client device 220, may attach a query to a medical term that the medical coder is unable to manually code). For example, the medical coder may attach the query "I don't know how to code this" to the medical term "Patient's hand is vibrating," and the medical coding consultant may respond by inputting query information that indicates that the valid code is "Parkinsonian Tremor."

Additionally, or alternatively, coding device 210 may automatically attach a query to a medical term (and/or similar medical terms) that cannot be automatically coded and cannot be manually coded based on input from a medical coder. Additionally, or alternatively, the medical coding consultant may read the query and respond to the query by inputting query information to client device 220 used by the medical coder or another client device 220 that is connected to coding device 210. Additionally, or alternatively, client device 220 may provide the query information to coding device 210, which may display the query information on the user interface of client device 220 being used by the medical coder. As described above in connection with block 640 of FIG. 6, the medical coder may input a newly input code based on reading the query information displayed on client device 220. In some implementations, in response to the query, the medical coding consultant may input a valid code directly into coding device 210.

In this way, coding device 210, using coding based on automatic dictionary updates and based on seeking matching medical codes for a medical term, may code the medical term with consistency and according to the latest demands of the regulatory environment.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7A:
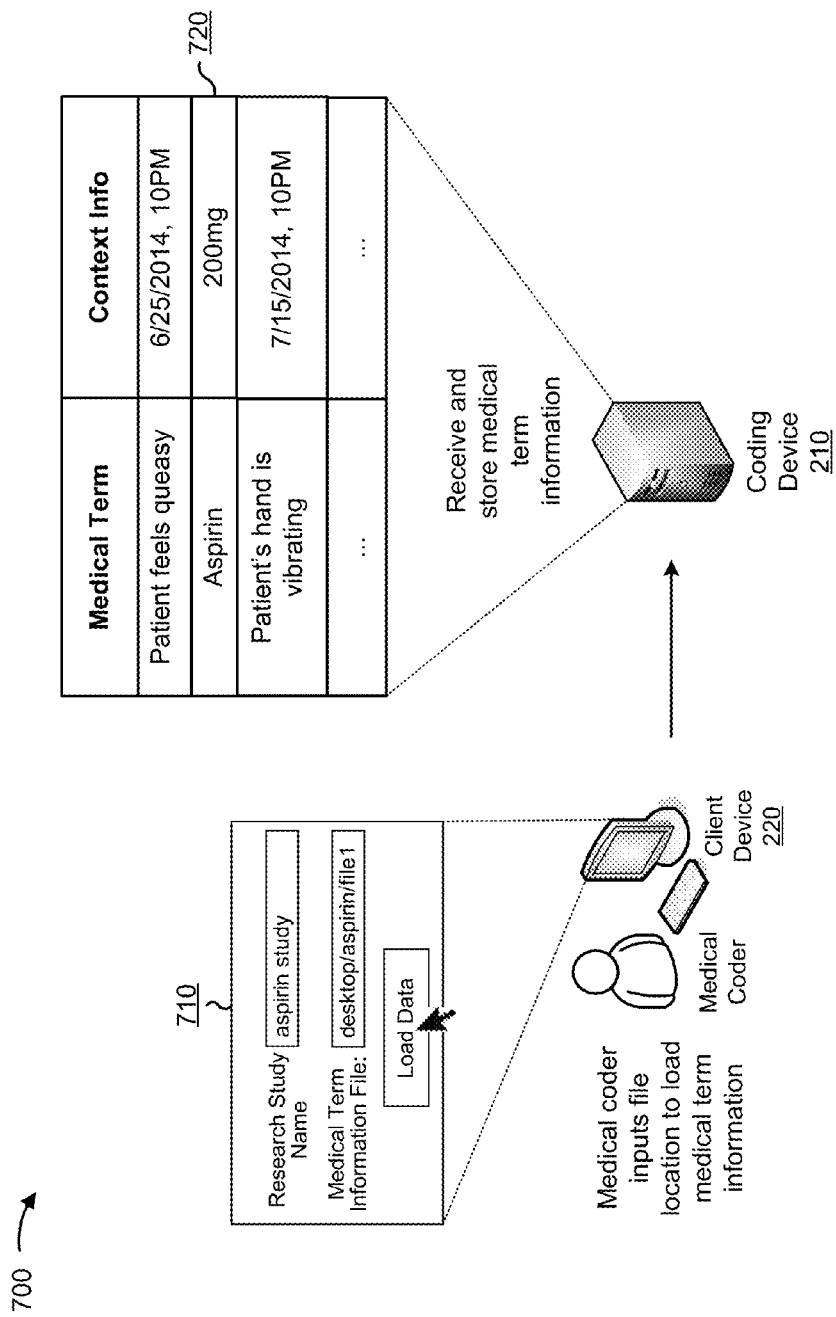
FIGS. 7A-7C are diagrams of an example implementation relating to the example process shown in FIG. 6.
Figure 7B:
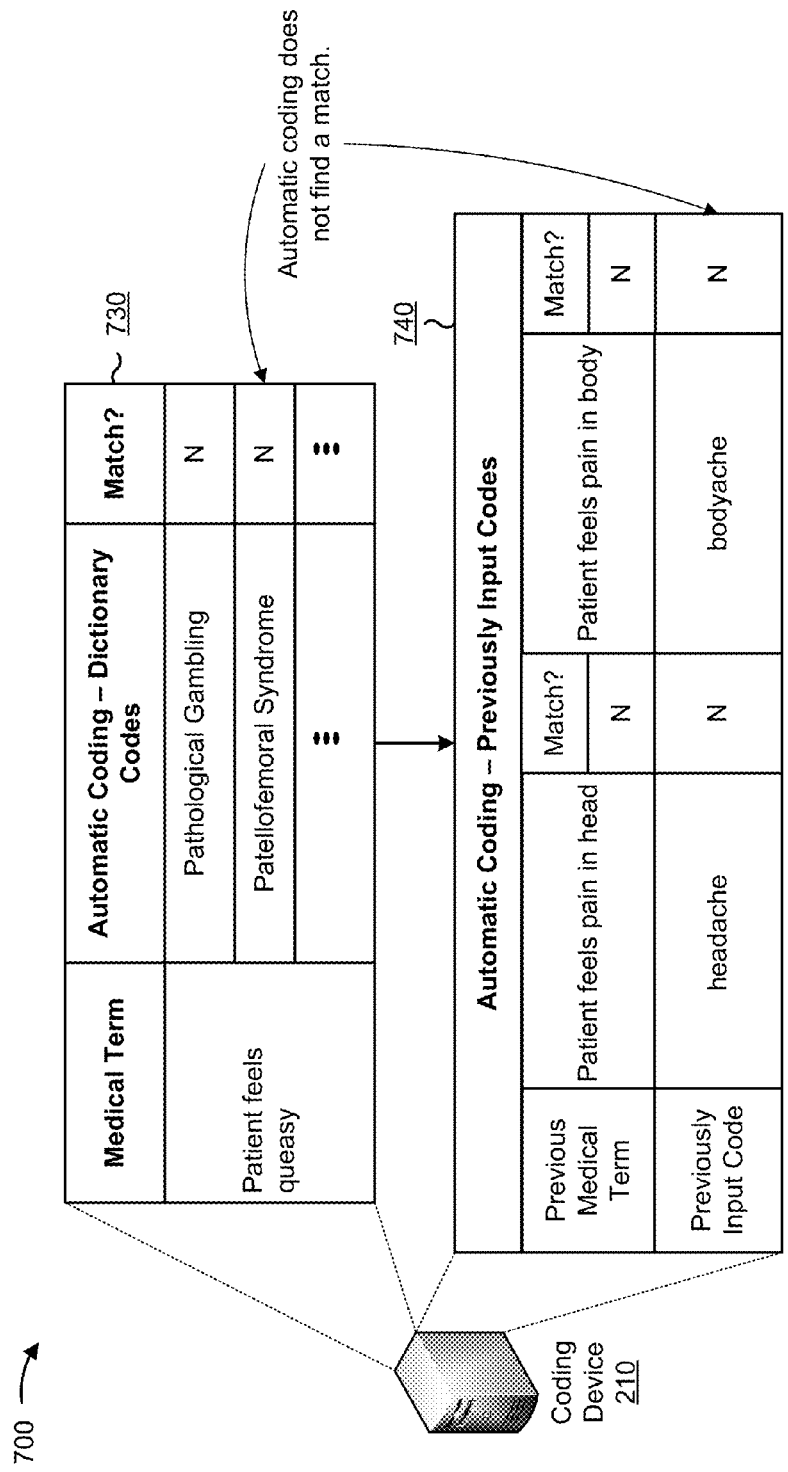
Figure 7C:
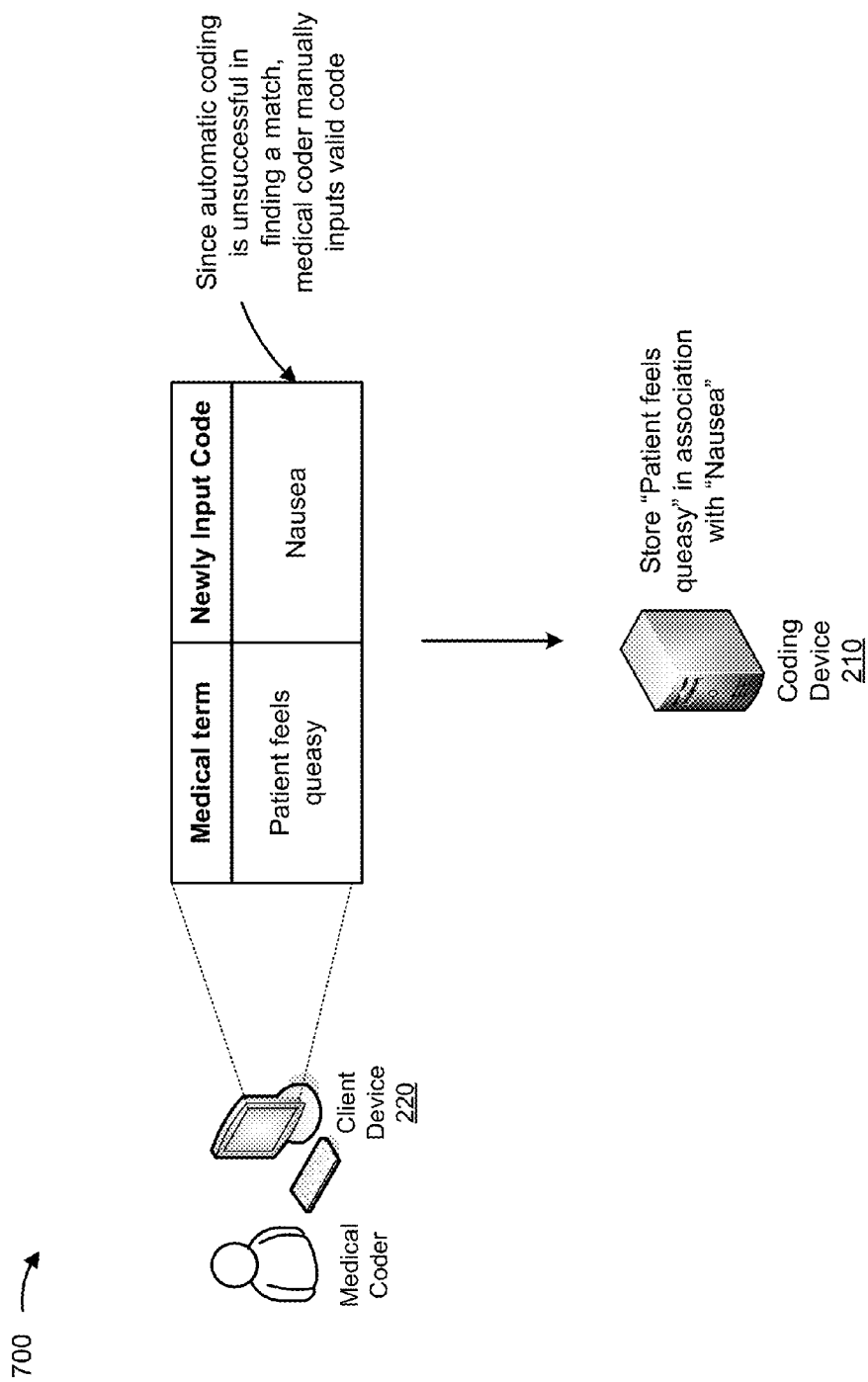

FIGS. 7A-7C are diagrams of an example implementation 700 relating to example process 600 shown in FIG. 6. FIGS. 7A-7C show an example of determining a medical code associated with a medical term and storing the medical code. Assume that example implementation 700 includes coding device 210 and client device 220.

As shown in FIG. 7A, a medical coder inputs, to client device 220, information that identifies a research study (e.g., shown as "aspirin study"), as shown by reference number 710. The medical coder also inputs, to client device 220, a location of a file that contains medical term information that identifies a medical term associated with the aspirin study (e.g., "desktop/aspirin/file1"). The medical coder clicks on the button labeled "load data," which instructs client device 220 to provide, to coding device 210, information that identifies the research study and the medical term information.

Coding device 210 receives the medical term information that identifies the medical term associated with the aspirin study. As shown in the data structure stored by coding device 210 (e.g., as shown by reference number 720), the medical term information includes the medical terms "Patient feels queasy," "Aspirin," "Patient's hand is vibrating," and so on. As further shown by reference number 720, the medical term information also includes context information associated with the medical terms (e.g., the time and date when "Patient feels queasy" was observed during the research study, the dosage of "Aspirin," the time and date when "Patient's hand is vibrating" was observed during the research study, etc.). Coding device 210 stores the medical term information so that a medical term, included in the medical term information, can be coded.

As shown in FIG. 7B, coding device 210 determines whether the medical term "Patient feels queasy" can be automatically coded based on dictionary codes and/or previously input codes.

As shown by reference number 730, coding device 210 determines that automatic coding based on the dictionary codes is not possible because "Patient feels queasy" does not match a dictionary code. As shown, coding device 210 searches for dictionary codes that are near "Patient feels queasy," in terms of alphabetical order (e.g., "pathological gambling," "patellofemoral syndrome," and so on), to determine that no dictionary code matches.

As shown by reference number 740, coding device 210 determines that automatic coding based on the previously input codes is not possible because "Patient feels queasy" does not match a previous medical term associated with a previously input code. Coding device 210 searches for previous medical terms near "Patient feels queasy," in terms of alphabetical order (e.g., Patient feels pain in head, Patient feels pain in body, and so on), to determine that no previously input code is associated with "Patient feels queasy."

Coding device 210 determines that the medical term information cannot be automatically coded because no dictionary code matches the medical term and because no previous medical term, associated with a previously input code, matches the medical term "Patient feels queasy."

As shown in FIG. 7C, since automatic coding is unsuccessful in finding a match, coding device 210 engages in a process of manual coding. Assume that coding device 210 determines that the medical term is to be manually coded based on an instruction from client device 220, which was sent as a result of input by the medical coder into client device 220.

As shown, coding device 210 receives, from client device 220, a newly input code (e.g., "Nausea") that is associated with "Patient feels queasy." Assume that the medical coder, based on the medical coder's own expertise, inputs the newly input code into client device 220, which provided the newly input code to coding device 210. Coding device 220 stores, in the data structure, "Nausea," as the valid code associated with the medical term "Patient feels queasy." Coding device 210 also stores, for future use during later iterations of coding, the association between the newly input code and the medical term (e.g., the next time coding device 210 receives the medical term "Patient feels queasy," coding device 210 will be able to automatically assign the code "Nausea" to the medical term). In this way, coding device 210 codes a medical term based on automatic coding that uses matches and based on manual coding that trains coding device 210 to code automatically in future iterations of coding.

As indicated above, FIGS. 7A-7C are provided merely as an example. Other examples are possible and may differ from what was described with regard to FIGS. 7A-7C.

Figure 8A:
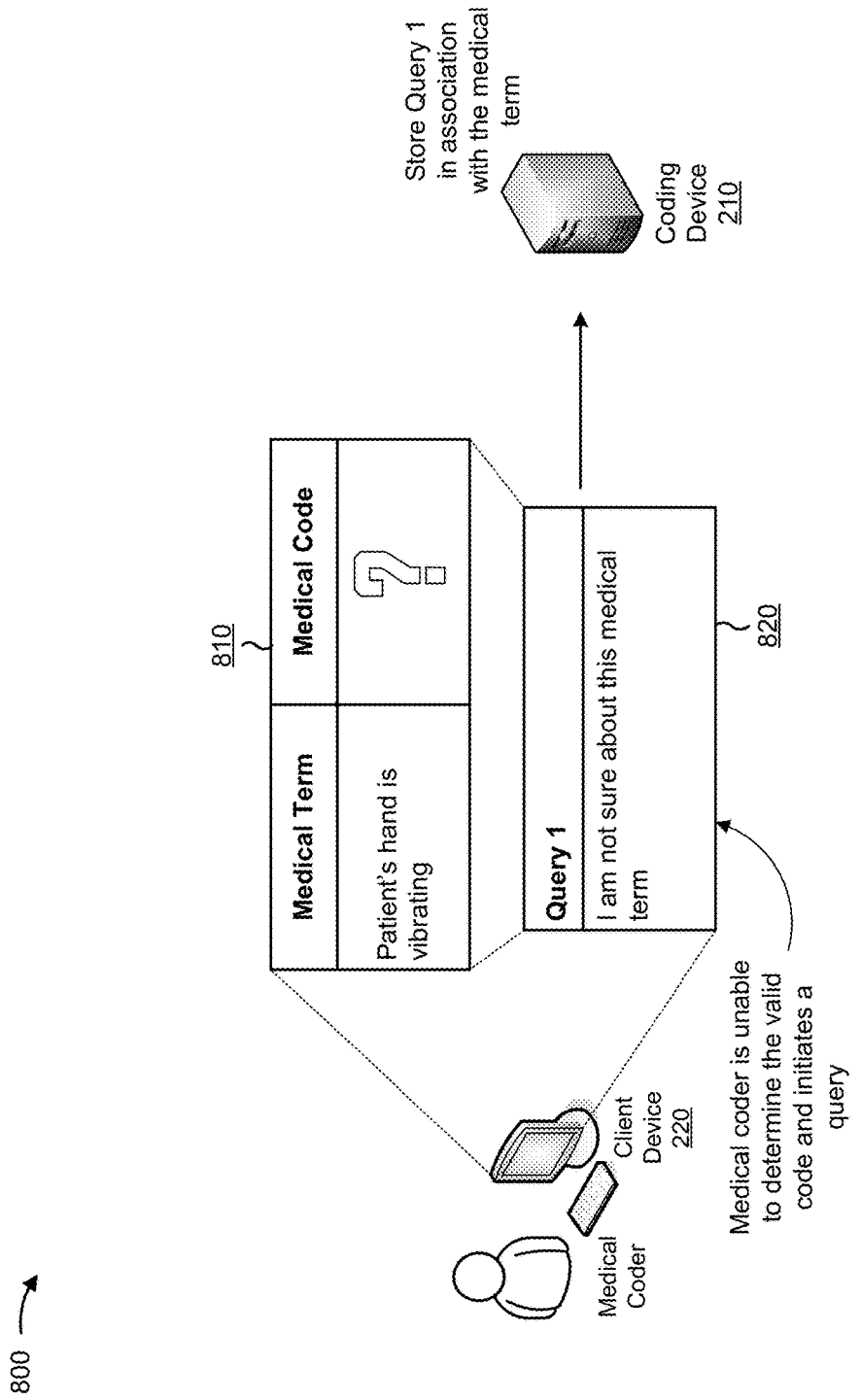
FIGS. 8A and 8B are diagrams of another example implementation relating to the example process shown in FIG. 6.
Figure 8B:
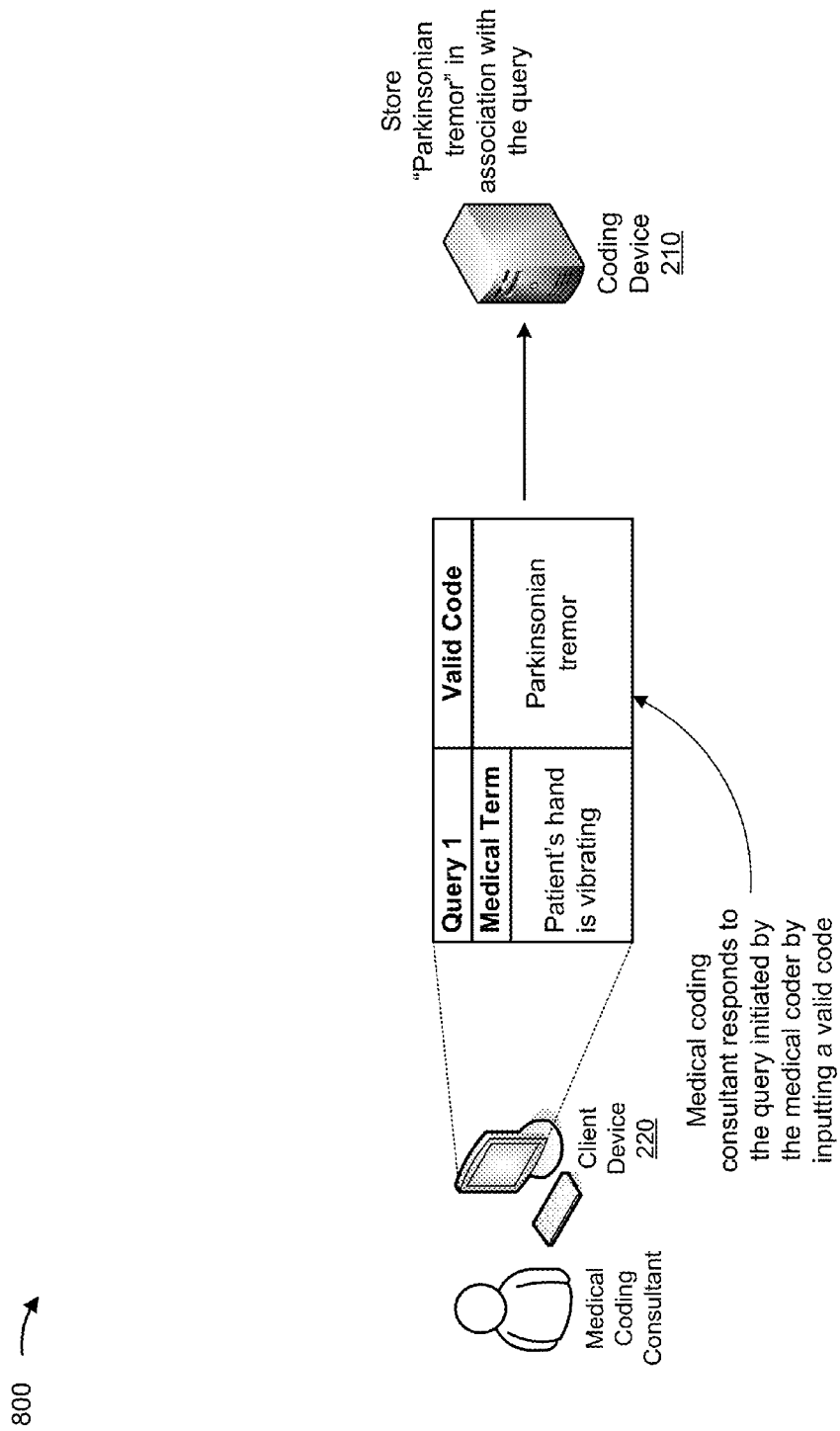

FIGS. 8A and 8B are diagrams of an example implementation 800 relating to example process 600 shown in FIG. 6. FIGS. 8A and 8B show an example of determining, using query information, a medical code associated with a medical term and storing the medical code in the data structure. Assume that example implementation 800 includes coding device 210 and client device 220.

As shown in FIG. 8A, a user interface displayed by client device 220 may be visible to a medical coder. Assume further that coding device 210 has received information that identifies a research study and has received medical term information. Assume further that the medical term information includes a medical term "Patient's hand is vibrating." Assume further that coding device 210 has determined that the medical term cannot be automatically coded.

Client device 220 displays, on a user interface, the medical term "Patient's hand is vibrating" and an indication that the medical term cannot be automatically coded, after receiving an instruction from coding device 210 that the medical term cannot be automatically coded. As shown, the medical coder is unable to determine a medical code associated with the medical term (e.g., as shown by reference number 810) and initiates a query associated with the medical term. As shown by reference number 820, the medical coder inputs a text "I am not sure about this medical term" to client device 220, which provides the text to coding device 210, which inserts the text into the query and stores the query in the data structure.

As shown in FIG. 8B, a user interface displayed by another client device 220 is used by a medical coding consultant (first client device 220 is used by the medical coder and second client device 220 is used by the medical coding consultant). The medical coding consultant views the user interface and sees an indication that there is a query attached to (e.g., associated with) the medical term "Patient's hand is vibrating." The medical coding consultant may provide an input into second client device 220, which may provide coding device 210 with a newly input code that is the valid code (e.g., "Parkinsonian tremor" is the newly input code for the medical term "Patient's hand is vibrating"). The medical coding consultant may provide an input that is the valid code based on the medical coding consultant's expertise, based on studying a patient medical record, based on performing research, or the like. Coding device 220 stores, in the data structure, "Parkinsonian tremor," as the valid code associated with the medical term "Patient's hand is vibrating." Coding device 220 also stores, for future use during later iterations of coding of medical terms, the association between the newly input code and the medical term.

In this way, coding device 210, using coding based on seeking matching medical codes for a medical term and using a user-friendly query interface, may code the medical term with consistency and according to stringent demands of the regulatory context.

As indicated above, FIGS. 8A and 8B are provided merely as an example. Other examples are possible and may differ from what was described with regard to FIGS. 8A and 8B.

FIG. 9 is a flow chart of an example process 900 for creating a coding report and/or updating the data structure based on the coding report. In some implementations, one or more process blocks of FIG. 9 may be performed by coding device 210. In some implementations, one or more process blocks of FIG. 9 may be performed by another device or a set of devices separate from or including coding device 210, such as client device 220.

As shown in FIG. 9, process 900 may include creating a coding report based on receiving one or more parameters associated with the coding report (block 910). For example, coding device 210 may create a coding report based on receiving parameters associated with the coding report. Parameters associated with the coding report may include pre-configured parameters to create pre-configured reports and/or custom parameters received from client device 220 to create customized reports. The parameters associated with the coding report may include information that identifies a research study and/or information that identifies a dictionary. In some implementations, a medical coding consultant may select, via the user interface of client device 220, pre-configured parameters associated with a pre-configured report. Additionally, or alternatively, coding device 210 may receive the pre-configured parameters and create the coding report based on the pre-configured parameters.

For example, the pre-configured reports may include a coding consistency report (e.g., a report that may display a medical term and an associated medical code, along with the frequency with which the medical code is assigned to the medical term), a coded report-unique (e.g., a report that lists medical terms and their associated medical codes organized by medical term), a coded report-patient level (e.g., a report that lists medical terms and their associated medical codes organized by patient), an uncoded report-unique (e.g. a report that lists uncoded medical terms organized by medical term), an uncoded report-patient level (e.g. a report that lists uncoded medical terms organized by patient), an audit report (e.g., a report that lists every change made by every user organized by medical term, medical code, patient, time of change, or the like), or the like.

In some implementations, the medical coding consultant may input, into client device 220, an instruction that includes custom parameters associated with a customized report. For example, the medical coding consultant may input an instruction that includes parameters that are associated with a coding consistency report that covers coding performed during a limited period of time. Additionally, or alternatively, coding device 210 may receive the custom parameters and create the coding report based on the custom parameters.

As further shown in FIG. 9, process 900 may include determining whether there is an inconsistency in coding (block 920). For example, coding device 210 may determine whether there is an inconsistency in coding based on an instruction from client device 220 and/or based on automatically analyzing a report. For example, coding device 210 may analyze a coding inconsistency report and determine that there is an inconsistency in coding because more than one medical code has been assigned to a medical term (e.g., different medical coders have manually assigned different medical codes to the same medical term because of an error of judgment, a lack of information, or other human error). In some implementations, the medical coding consultant may inspect, via the user interface of client device 220, a coding report-unique, an audit report, or the like, to determine whether there is an inconsistency in coding. Additionally, or alternatively, the medical coding consultant may determine there is an inconsistency in coding if more than one medical code has been assigned to (e.g., is associated with) a medical term.

As further shown in FIG. 9, if there is no inconsistency in coding (block 920—NO), then process 900 may include providing a notification that the coding meets quality control standards (block 930). For example, if there is no inconsistency in coding, coding device 210 may provide, to client device 220, a notification that the coding meets quality control standards. Additionally, or alternatively, client device 220 may display the notification on the user interface and the medical coding consultant may take appropriate action such as submitting the coded medical term information to a regulatory authority, providing the coded medical term information to an academic journal in connection with a peer review process, or the like. In some implementations, if there is an inconsistency in coding, the inconsistency may be resolved in order to meet quality control standards (as described below in connection with blocks 940 and 950 of FIG. 9), and coding device 210 may provide a notification that the coding meets quality control standards after the inconsistency has been resolved.

As further shown in FIG. 9, if there is an inconsistency in coding (block 920—YES), then process 900 may include receiving information that resolves the inconsistency and recoding a medical term based on the information (block 940). For example, if there is an inconsistency in coding, coding device 210 may receive information that resolves the inconsistency from client device 220 and/or may re-code a medical term based on the information. In some implementations, if there is an inconsistency in coding, coding device 210 may provide a notification to client device 220 that indicates the inconsistency. Additionally, or alternatively, the medical coding consultant, in response to the notification, may input information that resolves the inconsistency into client device 220, which may provide the information to coding device 210.

For example, coding device 210 may determine there is an inconsistency because more than one "valid" code is associated with a medical term, according to a coding consistency report. In such an example, the medical coding consultant may input an instruction that includes the correct "valid" code (e.g., the verified medical code as determined by a medical coding consultant using report analytics) associated with the medical term. Coding device 210 may receive the verified code from client device 220 and may re-code the medical term (e.g., may update the data structure as many times as the medical term and the medical code associated with the medical term appears in the data structure) in such a manner that the medical term is to be associated with the verified code.

In some implementations, coding device 210 may determine a verified code based on performing an analysis of valid codes associated with the medical term. Additionally, or alternatively, the analysis may be based on seniority (e.g., expert level) of a user who provided a valid code, a frequency with which the valid code is associated with the medical term, a date of entry of the valid code, or the like. Additionally, or alternatively, coding device 210 may suggest the verified code, determined through the analysis, to the medical coding consultant and seek a confirmation from the medical coding consultant (e.g., a confirmation that the verified code accurately codes the medical term).

As further shown in FIG. 9, process 900 may include updating the data structure based on the information (block 950). For example, coding device 210 may update the data structure, based on the information that resolves the inconsistency, in order to improve future coding. In some implementations, coding device 210 may update the data structure, based on the information, in a manner that allows coding device 210 to access the information during future iterations of automatic coding. For example, coding device 210 may automatically code the medical term with the verified code if coding device 210 receives the medical term for coding in the future.

In some implementations, after updating the data structure, coding device 210 may provide a notification that indicates that the coding meets quality control standards (as described above in connection with block 930 of FIG. 9). In this way, coding device 210 may create a coding report and/or may update the data structure based on the coding report in order to improve the consistency of already coded medical terms and to improve the consistency of medical terms to be coded in the future.

Although FIG. 9 shows example blocks of process 900, in some implementations, process 900 may include additional blocks, fewer blocks, different blocks, or differently arranged blocks than those depicted in FIG. 9. Additionally, or alternatively, two or more of the blocks of process 900 may be performed in parallel.

Figure 10A:
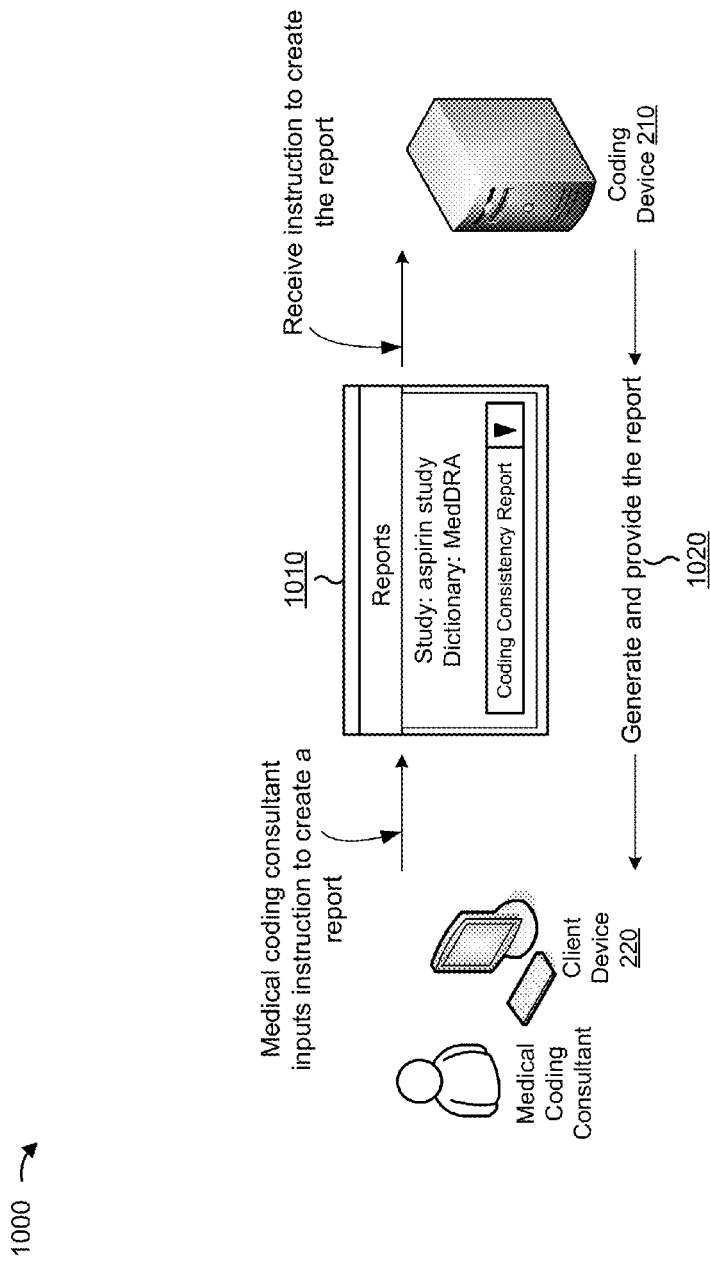
FIGS. 10A and 10B are diagrams of an example implementation relating to the example process shown in FIG. 9.
Figure 10B:
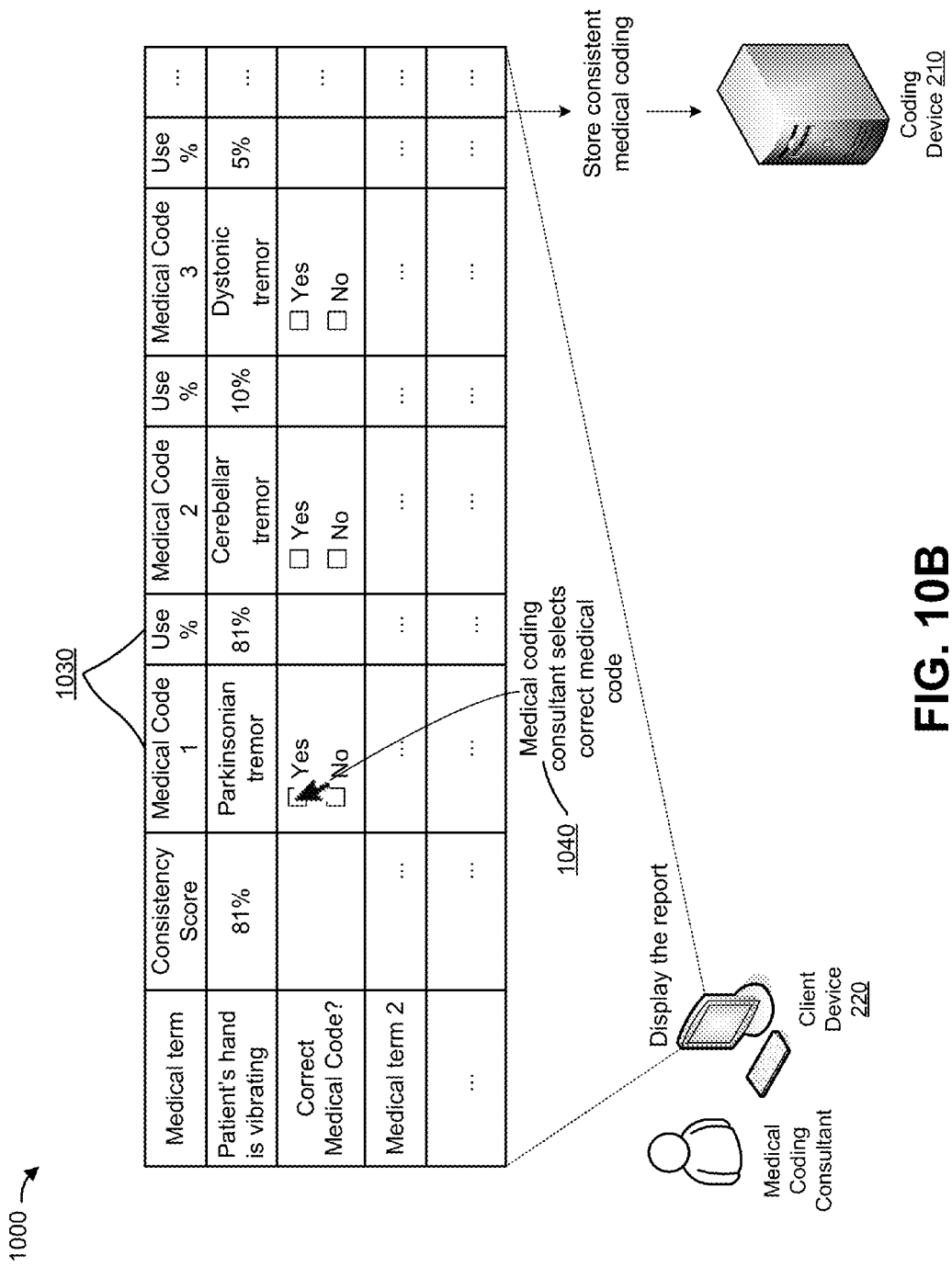

FIGS. 10A and 10B are diagrams of an example implementation 1000 relating to example process 900 shown in FIG. 9. FIGS. 10A and 10B show an example of creating a coding report and/or updating the data structure based on the coding report. Assume that example implementation 1000 includes a coding device 210 and a client device 220. Assume further that coding device 210 has created a data structure that is used for storing medical term information that identifies one or more medical terms. Assume further that coding device 210 has determined one or more medical codes associated with the one or more medical terms.

As shown in FIG. 10A, a medical coding consultant inputs an instruction into client device 220, which includes parameters associated with creating a report. The parameters are associated with a pre-configured report (e.g., the parameters include information that identifies that a coding consistency report is to be created for the aspirin study in connection with MedDRA). As shown by reference number 1010, coding device 210 receives the instruction that includes the parameters associated with creating the coding consistency report. As further shown, coding device 210 creates a coding consistency report based on receiving parameters from client device 220. As shown by reference number 1020, coding device 210 provides the report to client device 220 for display on the user interface of client device 220.

As shown in FIG. 10B, the coding consistency report is displayed by client device 220. As shown by reference number 1030, the report includes a medical term (e.g., shown as "Patient's hand is vibrating") and a consistency score associated with the medical term (e.g., shown as 81%). The consistency score is the percentage of times the most commonly used medical code was used. In addition, the coding consistency report includes other medical codes associated with the medical term and the percentage of times the other medical codes were used out of all the instances when the medical term appears in the data structure.

As shown, for the medical term "Patient's hand is vibrating," the medical code "Parkinsonian tremor" was used 81% of the time, the medical code "Cerebellar tremor" was used 10% of the time, and the medical code "Dystonic tremor" was used 5% of the time. In addition, the coding consistency report includes other, less commonly used medical codes (not shown), and other medical terms (not shown). Different medical codes for the same medical term may have been used because different medical coders may have assigned, using client device 220, different medical codes to the same medical term during manual coding. Different medical coders may have assigned different medical codes to a medical term because of a lapse in judgment, a lack of experience, or the like.

As shown by reference number 1040, in response to viewing the coding consistency report, the medical coding consultant, using client device 220, selects the correct medical code (e.g., a verified code) out of the most commonly used medical codes. As shown, the verified code, associated with the medical term "Patient's hand is vibrating" is "Parkinsonian tremor." Coding device 210 re-codes the medical term using the verified code wherever the medical term appears in the data structure. In addition, coding device 210 updates the data structure based on the verified code in order to improve future coding (e.g., in order to use the verified code the next time coding device 210 receives the medical term for coding). In this way, coding device 210 creates a coding report and/or updates the data structure based on the coding report in order to improve the consistency of already coded medical terms and to improve the consistency of medical terms to be coded in the future.

As indicated above, FIGS. 10A and 10B are provided merely as an example. Other examples are possible and may differ from what was described with regard to FIGS. 10A and 10B.

Implementations described herein may include a coding device that may automatically create and/or test one or more data structures, may be able to update stored codes during a dictionary update, may be able to code context information, may selectively auto-code a medical term based on exact matching, may attach queries to a medical term included in a user interface, may create reports, and/or may update the one or more data structures based on the reports. Implementations described herein may improve accuracy and consistency of medical coding, thereby improving accuracy of medical records used during a drug-approval regulatory process and thus, improving public health.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A computer-readable medium storing instructions, the instructions comprising:
   one or more instructions that, when executed by one or more processors, cause the one or more processors to:
      receive information that identifies a first medical term, the first medical term being associated with a research study;
      select a data structure, of a plurality of data structures, associated with the research study,
         the data structure being configured for receiving data;
      determine whether the first medical term includes corrupted data,
         the first medical term being placed at a preliminary location within the data
      structure to prevent the first medical term from contaminating other non-corrupt data stored in the data structure until the first medical term is determined to be non-corrupt;
      selectively store the first medical term in the data structure based on determining whether the first medical term includes the corrupted data,
         the first medical term not being stored in the data structure when the first medical term includes the corrupted data,
         the first medical term being stored in the data structure at a location different from the preliminary location within the data structure when the first medical term does not include the corrupted data,
      provide a user interface to change the corrupted data,
      receive, via the user interface, the change to the corrupted data,
         the change causing the corrupted data to be non-corrupt,
      determine whether the first medical term is associated with a first medical code,
         the first medical code being a medical code previously input by a first user in association with a second medical term, or
         the first medical code being included in a dictionary stored by the data structure;
      determine a valid code associated with the first medical term based on determining whether the first medical term is associated with the first medical code,
         the valid code being determined based on the first medical code when the first medical term is associated with the first medical code,
         the valid code being determined based on a second medical code, input by a second user, when the first medical term is not associated with the first medical code;
      automatically attach a query to the first medical term if the valid code cannot be determined based on the first medical code or the second medical code,
         the query being provided to a third user,
         the third user inputting query information associated with a new medical code;
      provide information that identifies the valid code; and
      update the data structure based upon determining the valid code to improve consistency of previously coded medical terms.

2. The computer-readable medium of claim 1, where the one or more instructions, when executed by the one or more processors, further cause the one or more processors to:

receive information that identifies the dictionary; and
create the data structure based on the dictionary.

3. The computer-readable medium of claim 1, where the one or more instructions, that cause the one or more processors to determine whether the first medical term is associated with the first medical code, further cause the one or more processors to:
determine that the first medical term matches the second medical term or is included in the dictionary; and
determine that the first medical term is associated with the first medical code based on determining that the first medical term matches the second medical term or is included in the dictionary.

4. The computer-readable medium of claim 1, where the one or more instructions, when executed by the one or more processors, further cause the one or more processors to:
determine, using the data structure, that the first medical term is associated with a plurality of valid codes,
the plurality of valid codes including the valid code;
provide, based on determining that the first medical term is associated with the plurality of valid codes, a report that includes the first medical term and the plurality of valid codes associated with the first medical term;
receive, from the third user, a verified code that is associated with the first medical term,
the verified code being one of the plurality of valid codes; and
store, in the data structure, an association between the verified code and the first medical term.

5. The computer-readable medium of claim 1, where the one or more instructions, when executed by the one or more processors, further cause the one or more processors to:
determine, using the data structure, that the first medical term is associated with a single valid code; and
provide, based on determining that the first medical term is associated with the single valid code, a report that includes an indication that quality control standards have been satisfied.

6. The computer-readable medium of claim 1, where the one or more instructions, when executed by the one or more processors, further cause the one or more processors to:
receive a dictionary update to the dictionary; and
update the data structure based on receiving the dictionary update by replacing the first medical code with another new medical code, included in the dictionary update, that corresponds to the first medical code.

7. A method, comprising:
receiving, by a device, information that identifies a first medical term,
the first medical term being associated with a research study;
selecting, by the device, a data structure, of a plurality of data structures, associated with the research study,
the data structure being configured for receiving data;
determining, by the device, whether the first medical term includes corrupted data,
the first medical term being placed at a preliminary location within the data structure to prevent the first medical term from contaminating other non-corrupt data stored in the data structure until the first medical term is determined to be non-corrupt;
selectively storing, by the device, the first medical term in the data structure based on determining whether the first medical term includes the corrupted data,
the first medical term not being stored in the data structure when the first medical term includes the corrupted data,
the first medical term being stored in the data structure at a location different from the preliminary location within the data structure when the first medical term does not include the corrupted data;
providing, by the device, a user interface to change the corrupted data;
receiving, by the device and via the user interface, the change to the corrupted data,
the change causing the corrupted data to be non-corrupt;
determining, by the device, whether the first medical term matches a second medical term, associated with a first medical code, or a second medical code,
the first medical code being a medical code previously input by a first user in association with the second medical term,
the second medical code being included in a dictionary stored by the data structure;
determining, by the device, a valid code associated with the first medical term based on determining whether the first medical term matches the second medical term or the second medical code,
the valid code being determined based on the second medical term or the second medical code when the first medical term matches the second medical term or the second medical code,
the valid code being determined based on a third medical code, input by a second user, when the first medical term does not match the second medical term or the second medical code;
automatically attaching, by the device, a query to the first medical term if the valid code cannot be determined based on the second medical code or the third medical code,
the query being provided to a third user,
the third user inputting query information associated with a new medical code;
providing, by the device, information that identifies the valid code; and
updating, by the device, the data structure based upon determining the valid code to improve consistency of previously coded medical terms.

8. The method of claim 7, further comprising:
determining, using the data structure, that the first medical term is associated with a plurality of valid codes,
the plurality of valid codes including the valid code;
providing, based on determining that the first medical term is associated with the plurality of valid codes, a report that includes the first medical term and the plurality of valid codes associated with the first medical term;
receiving, from the third user, a verified code that is associated with the first medical term,
the verified code being one of the plurality of valid codes; and
storing, in the data structure, an association between the verified code and the first medical term.

9. The method of claim 7, where the first medical term includes at least one of:
information that identifies a drug;
information that identifies an effect experienced by a patient after taking the drug; or
information related to the drug or the effect.

10. The method of claim 7, where the first medical code, the second medical code, the third medical code, and the valid code include at least one of:
a standardized name of a drug;

a standardized name of an effect experienced by a patient after taking the drug; or a standardized version of medical information related to the drug or the effect.

11. The method of claim 7, where receiving the information that identifies the first medical term further comprises:

storing, in the data structure, the valid code in association with the first medical term when the valid code is determined based on the third medical code.

12. The method of claim 7, where receiving the information that identifies the first medical term further comprises:

receiving context information that identifies a route of entry of a drug or a purpose of the drug, the route of entry of the drug being a method used by a patient to take the drug, and the purpose of the drug being one or more reasons the patient is taking the drug; and storing the context information in association with the first medical term.

13. The method of claim 7, further comprising:

determining, using the data structure, that the first medical term is associated with a single valid code; and providing, based on determining that the first medical term is associated with the single valid code, a report that includes an indication that quality control standards have been satisfied.

14. A device, comprising:

one or more memories; and one or more processors, communicatively coupled to the one or more memories, to:

receive information that identifies a first medical term, the first medical term being associated with a research study;

select a data structure, of a plurality of data structures, associated with the research study, the data structure being configured for receiving data;

determine whether the first medical term includes corrupted data, the first medical term being placed at a preliminary location within the data structure to prevent the first medical term from contaminating other non-corrupt data stored in the data structure until the first medical term is determined to be non-corrupt;

selectively store the first medical term in the data structure based on determining whether the first medical term includes the corrupted data, the first medical term not being stored in the data structure when the first medical term includes the corrupted data, the first medical term being stored in the data structure at a location different from the preliminary location within the data structure when the first medical term does not include the corrupted data;

provide a user interface to change the corrupted data;

receive, via the user interface, the change to the corrupted data, the change causing the corrupted data to be non-corrupt;

determine whether the first medical term is associated with a first medical code, the first medical code being a medical code previously input by a first user in association with a second medical term, or the first medical code being included in a dictionary stored by the data structure;

determine a valid code associated with the first medical term based on determining whether the first medical term is associated with the first medical code, the valid code being determined based on the first medical code when the first medical term is associated with the first medical code, the valid code being determined based on a second medical code, input by a second user, when the first medical term is not associated with the first medical code;

automatically attach a query to the first medical term if the valid code cannot be determined based on the first medical code or the second medical code, the query being provided to a third user, the third user inputting query information associated with a new medical code;

provide information that identifies the valid code in association with the first medical term; and update the data structure based upon determining the valid code to improve consistency of previously coded medical terms.

15. The device of claim 14, where the one or more processors, are further to:

determine, using the data structure, that the first medical term is associated with a plurality of valid codes, the plurality of valid codes including the valid code;

provide, based on determining that the first medical term is associated with the plurality of valid codes, a report that includes the first medical term and the plurality of valid codes associated with the first medical term;

receive, from the third user, a verified code that is associated with the first medical term, the verified code being one of the plurality of valid codes; and store, in the data structure, an association between the verified code and the first medical term.

16. The device of claim 14, where the one or more processors, when determining whether the first medical term is associated with the first medical code, are further to:

determine that the first medical term matches the second medical term or is included in the dictionary; and determine that the first medical term is associated with the first medical code based on determining that the first medical term matches the second medical term or is included in the dictionary.

17. The device of claim 14, where the one or more processors, when receiving the information that identifies the first medical term, are further to:

determine that a quantity of medical terms available for coding satisfies a threshold; and receive the information that identifies the first medical term based on determining that the quantity of medical terms available for coding satisfies the threshold.

18. The device of claim 14, where the one or more processors, when receiving the information that identifies the first medical term, are further to:

determine that an amount of time, which has passed since medical term information was last received, satisfies a threshold; and receive the information that identifies the first medical term based on determining that the amount of time satisfies the threshold.

19. The device of claim 14, where the one or more processors, when determining whether the first medical term is associated with the first medical code, are further to:

receive a dictionary update to the dictionary; and update the data structure based on receiving the dictionary update by replacing the first medical code with another new medical code, included in the dictionary update, that corresponds to the first medical code.

20. The computer-readable medium of claim 1, where the one or more instructions, that cause the one or more processors to receive information identifying the first medical term, further cause the one or more processors to:

receive context information that identifies a route of entry of a drug or a purpose of the drug,
the route of entry of the drug being a method used by a patient to take the drug, and
the purpose of the drug being one or more reasons the patient is taking the drug; and
store the context information in association with the first medical term.

* * * * *